(12) United States Patent
Nakaya

(10) Patent No.: US 7,790,107 B2
(45) Date of Patent: Sep. 7, 2010

(54) SAMPLE IMAGE OBTAINING APPARATUS, SAMPLE IMAGE OBTAINING SYSTEM, AND METHOD FOR OBTAINING SAMPLE IMAGE

(75) Inventor: Masanori Nakaya, Kobe (JP)

(73) Assignee: Sysmex Corporation, Kobe-shi (JP)

( * ) Notice: Subject to any disclaimer, the term of this patent is extended or adjusted under 35 U.S.C. 154(b) by 718 days.

(21) Appl. No.: 11/646,862

(22) Filed: Dec. 28, 2006

(65) Prior Publication Data

US 2007/0148046 A1 Jun. 28, 2007

(30) Foreign Application Priority Data

Dec. 28, 2005 (JP) ............................. 2005-376863

(51) Int. Cl.
*G01N 21/00* (2006.01)
(52) U.S. Cl. ............................. 422/65; 422/63; 422/64; 422/67; 422/99; 422/100; 436/43; 436/180
(58) Field of Classification Search ............. 422/63–65, 422/67, 99–10; 436/43, 180
See application file for complete search history.

(56) References Cited

U.S. PATENT DOCUMENTS

2003/0027342 A1* 2/2003 Sheridan et al. ............... 436/43

FOREIGN PATENT DOCUMENTS

JP 62-153727 7/1987

* cited by examiner

*Primary Examiner*—Jyoti Nagpaul
(74) *Attorney, Agent, or Firm*—Brinks Hofer Gilson & Lione

(57) ABSTRACT

The present invention is to present a sample image obtaining system that can manage a smear slide easily and perform the operation from the preparation of a smear slide to imaging efficiently. The sample image obtaining system comprises: a sample smearing means for smearing a sample on a slide glass; an identification information reading means for reading identification information of the sample smeared on the slide glass, the slide glass having the identification information; a sample image obtaining means for obtaining an image of the sample smeared on the slide glass; a storing means for storing the image obtained by the sample image obtaining means and the identification information read by the identification information reading means; and a slide glass transferring means for transferring the sample smeared slide glass from the sample smearing means to the sample image obtaining means.

14 Claims, 18 Drawing Sheets

SAMPLE IMAGE OBTAINING APPARATUS, SAMPLE IMAGE OBTAINING SYSTEM, AND METHOD FOR OBTAINING SAMPLE IMAGE

This application claims priority under 35 U.S.C. §119 to Japanese Patent Application No. JP2005-376863 filed Dec. 28, 2005, the entire content of which is hereby incorporated by reference.

FIELD OF THE INVENTION

The present invention relates to a sample image obtaining apparatus, a sample image obtaining system, and a method for obtaining a sample image. The present invention particularly relates to an apparatus, a system, and a method for obtaining an image of a sample smeared on a slide glass.

BACKGROUND OF THE INVENTION

A conventional apparatus for automatically classifying blood images by measuring blood smeared on a slide glass using a measuring unit that includes a microscope and the like is disclosed in Japanese Laid-Open Patent Publication No. 62-153727. In the apparatus for automatically classifying blood images disclosed in Japanese Laid-Open Patent Publication No. 62-153727, a smear slide prepared by smearing a sample on a slide glass is taken out from a cassette on a turntable mechanism by an take-out mechanism, and after the smear slide was moved to the entrance of a measuring unit by a slide moving lever, the measuring unit takes in the smear slide. Then, after the measuring operation was performed in the measuring unit and the smear slide was subsequently moved to the entrance of the measuring unit, the smear slide is returned from the measuring unit entrance to the cassette on the turntable mechanism by the slide moving lever.

In the apparatus for automatically classifying blood images disclosed in Japanese Laid-Open Patent Publication No. 62-153727, however, the smear slide is managed by the user. The user of the apparatus inputs beforehand the identification information that specifies the smear slide associated with the position of the smear slide within the cassette, and after measurement of the sample smeared on the slide glass, the user returns the smear slide to the original position that held the smear slide prior to measurement. Thus, time and labor are required to manage the smear slide which impedes examination efficiency. Furthermore, in the apparatus for automatically classifying blood images disclosed in Japanese Laid-Open Patent Publication No. 62-153727, the user must place the prepared smear slide in the cassette, and load the cassette containing the smear slide into the apparatus. Therefore, time and labor are required which impedes examination efficiency.

SUMMARY OF THE INVENTION

A first aspect of the present invention is a sample image obtaining apparatus, comprising: an identification information reader for reading identification information of a sample smeared on a slide glass, the slide glass having the identification information; an image obtainer for obtaining an image of the sample smeared on the slide glass; and a memory for storing the image obtained by the image obtainer and the identification information read by the identification information reader.

A second aspect of the present invention is a sample image obtaining system, comprising: a sample smearing apparatus for smearing a sample on a slide glass; a sample image obtaining apparatus for obtaining an image of the sample smeared on the slide glass; and a slide glass transferring apparatus for transferring the sample smeared slide glass obtained by the sample smearing apparatus to the sample image obtaining apparatus, wherein the sample image obtaining apparatus comprises an identification information reader for reading identification information of the sample smeared on the slide glass, the slide glass having the identification information; an image obtainer for obtaining the image of the sample smeared on the slide glass; and a memory for storing the image obtained by the image obtainer and the identification information read by the identification information reader.

A third aspect of the present invention is a sample image obtaining system, comprising: a sample smearing means for smearing a sample on a slide glass; an identification information reading means for reading identification information of the sample smeared on the slide glass, the slide glass having the identification information; a sample image obtaining means for obtaining an image of the sample smeared on the slide glass; a storing means for storing the image obtained by the sample image obtaining means and the identification information read by the identification information reading means; and a slide glass transferring means for transferring the sample smeared slide glass from the sample smearing means to the sample image obtaining means.

A fourth aspect of the present invention is A method for obtaining a sample image, comprising steps of: (a) smearing a sample on a slide glass; (b) reading identification information of the sample smeared on the slide glass; (c) automatically transferring the sample smeared slide glass to a sample image obtaining position; (d) obtaining an image of the sample smeared slide glass transferred to the sample image obtaining position; and (e) storing the image and the identification information.

DETAILED DESCRIPTION OF THE PREFERRED EMBODIMENT

The embodiments of the present invention are described hereinafter based on the drawings.

The structure of an embodiment of the sample image obtaining system of the present invention is first described referring to FIGS. 1 through 20.

Figure 1:
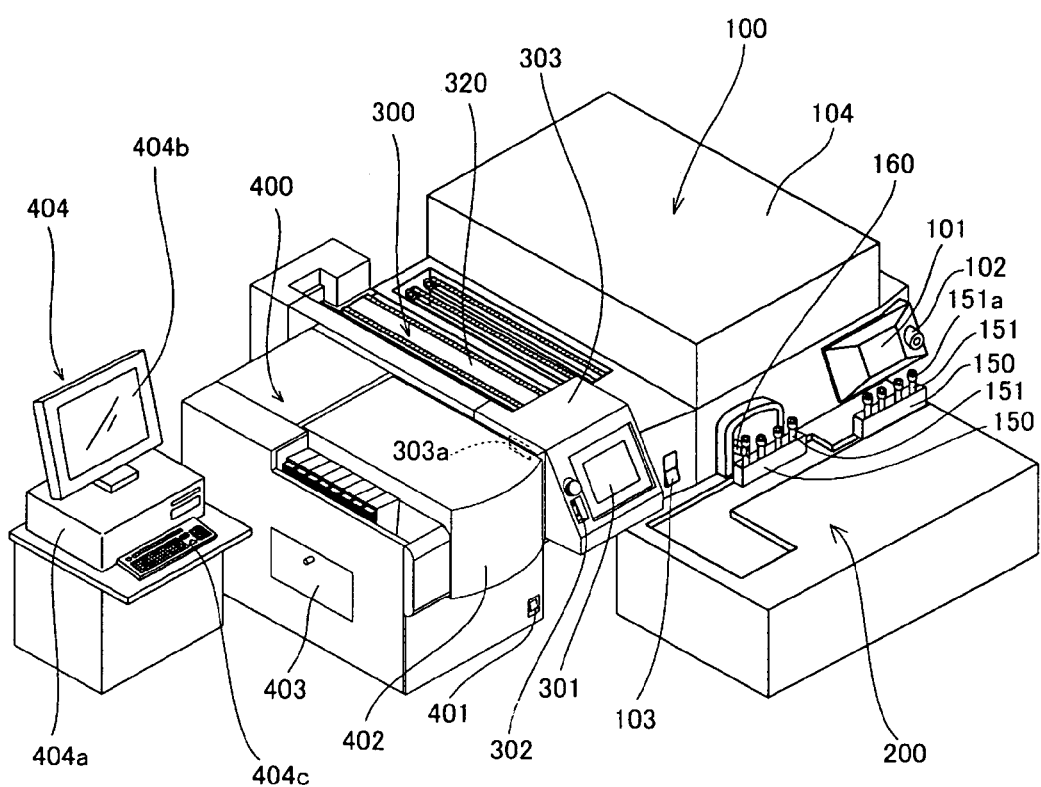
FIG. 1 is a perspective view showing the general structure of an embodiment of the sample image obtaining system of the present invention.
Figure 2:
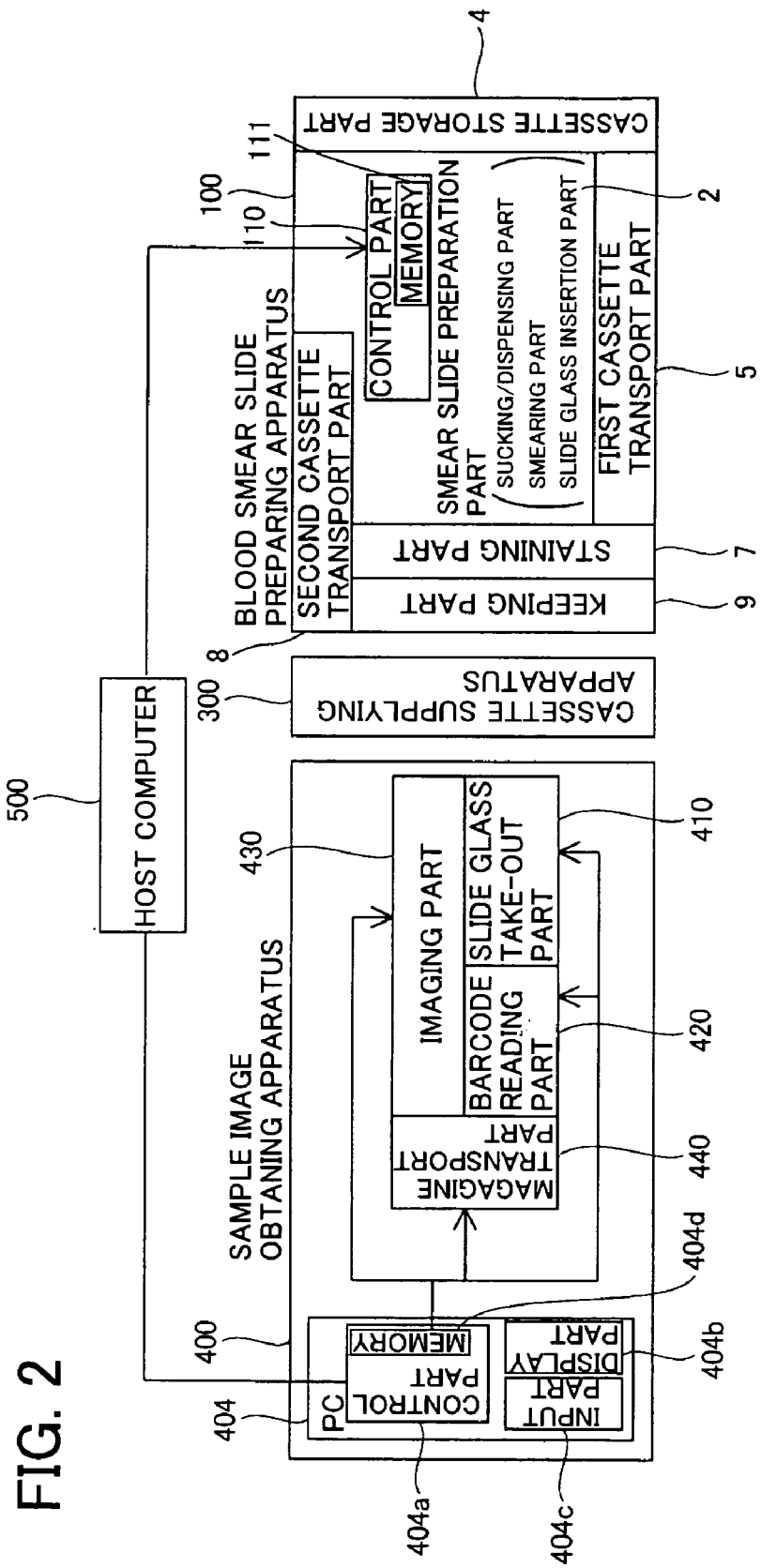
FIG. 2 is a block diagram of the embodiment of the sample image obtaining system shown in FIG. 1.

As shown in FIGS. 1 and 2, the embodiment of the sample image obtaining system of the present invention is configured by a blood smear slide preparing apparatus 100 for preparing a slide glass on which a blood sample is smeared, rack transporting apparatus 200, cassette supplying apparatus 300, sample image obtaining apparatus 400, and host computer 500. The sample image obtaining system subjects the image of a sample on a slide glass (slide glass 10 in FIG. 4) prepared by the blood smear slide preparing apparatus 100 to digital image processing, and automatically classifies the blood cells. Furthermore, the blood smear slide preparing apparatus 100 prepares two types of smear slides: a smear slide (slide glass) for automatic analysis, a sample on the slide glass can be analyzed by the sample image obtaining apparatus 400, and a smear slide (slide glass) for visual inspection, a sample on the slide glass can be analyzed visually. The blood smear slide preparing apparatus 100 has the processing capacity to prepare 120 blood smear slides per hour.

The rack transporting apparatus 200 is disposed in front of the blood smear slide preparing apparatus 100. The blood smear slide preparing apparatus 100, cassette supplying apparatus 300, and sample image obtaining apparatus 400 are aligned side by side.

As shown in FIG. 1, the rack transporting apparatus 200 is provided to automatically transport a sample rack 150 holding test tubes 151 containing blood to the blood smear slide preparing apparatus 100. The blood smear slide preparing apparatus 100 includes a touch panel-type display operating part 101, start switch 102, power switch 103, and cover 104. The blood smear slide preparing apparatus 100 is further provided with a hand member 160 for transporting a test tube 151 containing blood from the rack supplying apparatus 200 side to the blood smear slide preparing apparatus 100 side. A rubber stopper 151a seals the test tube 151 containing blood.

Figure 3:
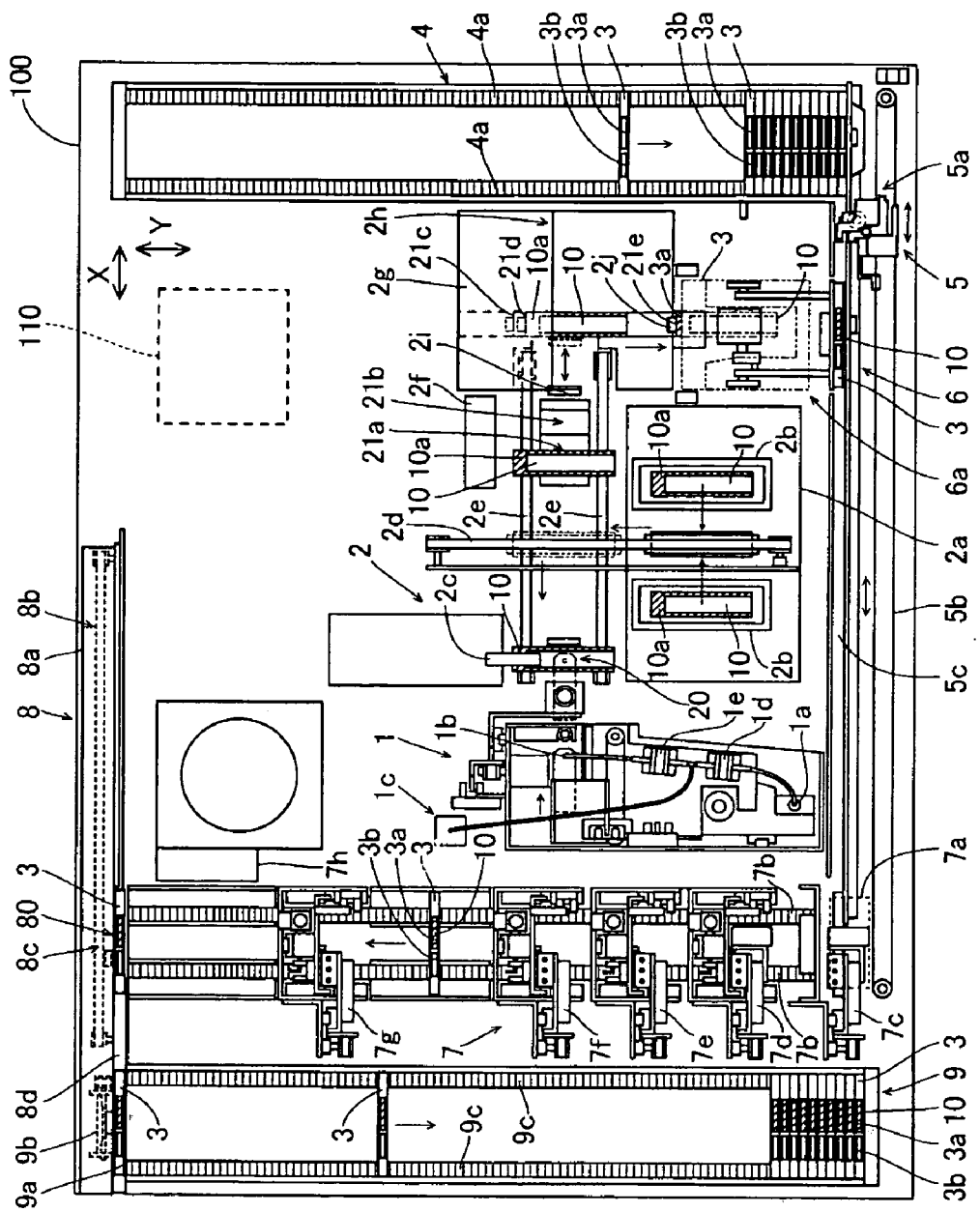
FIG. 3 is a plan view of the blood smear slide preparing apparatus of the embodiment of the sample image obtaining system shown in FIG. 1.

As shown in FIG. 3, the blood smear slide preparing apparatus 100 is provided with a sucking/dispensing part 1, smearing part 2, resin cassette 3, cassette storage part 4, first cassette transport part 5, slide glass insertion part 6, staining part 7, second cassette transport part 8, and keeping part 9.

The sucking/dispensing part 1 functions to both suck the blood from the test tube 151 (refer to FIG. 1) transported to the blood smear slide preparing apparatus 100 by the hand member 160 (refer to FIG. 1), and to drip the blood onto a slide glass 10. As shown in FIG. 3, the sucking/dispensing part 1 includes a piercer (sucking needle) 1a for sucking the blood from the test tube 151, pipette 1b for dispensing the blood on a slide glass 10, syringe pump 1c connected to the piercer 1a and pipette 1b, valve 1d for opening and closing the flow path between the piercer 1a and syringe pump 1c, and valve 1e for opening and closing the flow path between the pipette 1b and the syringe pump 1c. The sucking/dispensing part 1 functions to both dispense the same blood (sample) on each of two slide glasses 10, and to adjust the amount of blood to be dispensed for an amount corresponding to a smear slide for automatic analysis and an amount corresponding to a smear slide for visual inspection.

The smearing part 2 is provided to supply the slide glass 10 to the dispensing/smearing position 20, smear and dry the dripped blood on the slide glass 10, and print on the slide glass 10. The smearing part 2 is provided with a slide glass supplying part 2a, slide glass holding part 2b, drawing glass 2c, transport belts 2d and 2e, fan 2f, printing part 2g, and slide glass transporting part 2h.

The slide glass supplying part 2a has the function of supplying a slide glasses 10 held in two slide glass holding parts 2b onto a transport belt 2e using a take-out mechanism not shown in the drawing and chuck not shown in the drawing mounted on the transport belt 2d. The transport belt 2e is configured so as to transport slide glasses 10 to the dispensing/smearing position 20 and the drying positions 21a and 21b. The drawing glass 2c is configured so as to be movable to a position abutting the slide glass 10, and movable in the lengthwise direction of the slide glass 10, and is thus capable of smearing blood dispensed on the slide glass 10 at the dispensing/smearing position 20. The fan 2f is provided to dry the blood smeared on the slide glass 10 transported to the drying positions 21a and 21b.

Figure 4:
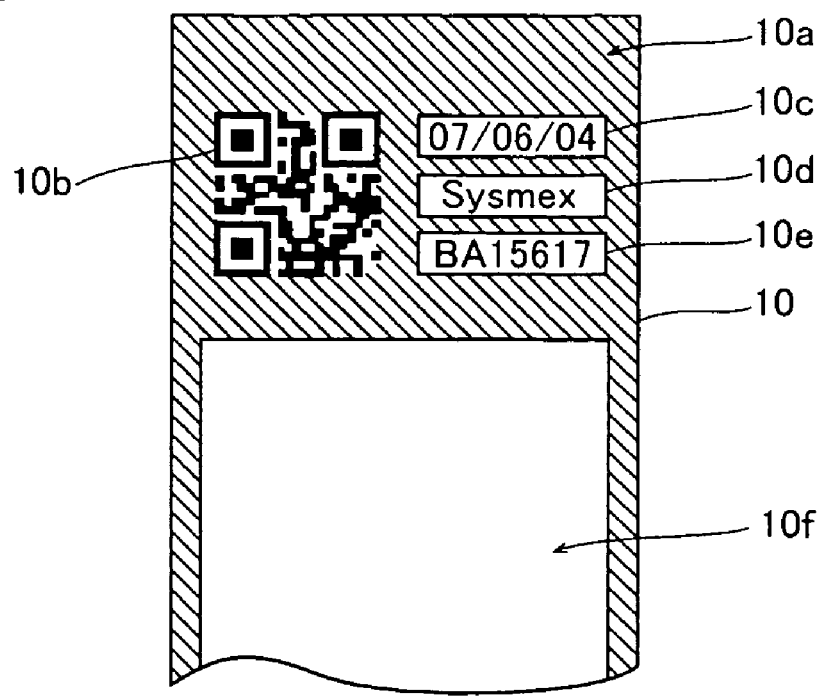
FIG. 4 is an enlarged view of a frosted region of the slide glass used in the embodiment of the sample image obtaining system shown in FIG. 1.

The printing part 2g is a thermal transfer printer. As shown in FIG. 4, the printing part 2g is provided to print a two-dimensional barcode 10b that stores sample information such as specimen number, date, reception number, patient name and the like, and to print three lines of text data of a date (Jul. 6, 2004) 10c, name (Sysmex) 10d, and sample number (BA15617) 10e as attribute information included in the sample information in a frosted region (information display region) 10a of the slide glass 10. The amount of information contained in the two-dimensional barcode in the present embodiment is 50 bytes.

As shown in FIG. 3, the slide glass transport part 2h is provided to move the slide glass 10 from the end of the transport belt 2e to the printing part 2g, and to move the printed slide glass 10 to the slide insertion position 21e into the cassette 3. The slide glass transport part 2h includes a horizontal moving piece 2i for moving the slide glass 10 in a horizontal direction (direct X in FIG. 3) from the end of the transport belt 2e to a horizontal position for printing, and a vertical moving piece 2j for moving the slide glass 10 in a vertical direction to a vertical position 21d for printing and a slide insertion position 21e into the cassette 3.

Figure 5:
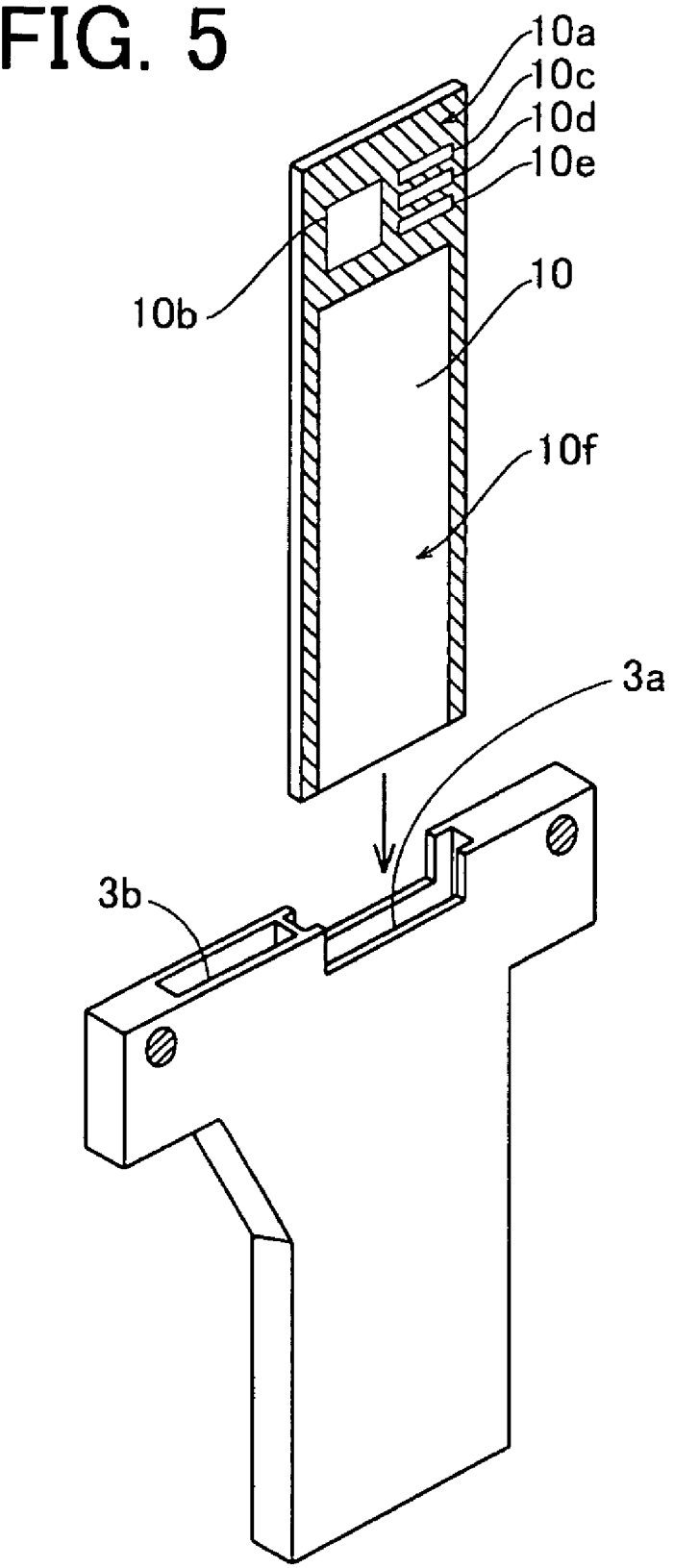
FIGS. 5 and 6 are perspective views of a slide glass and cassette used in the embodiment of the slide preparing and image obtaining system of FIG. 1.
Figure 6:
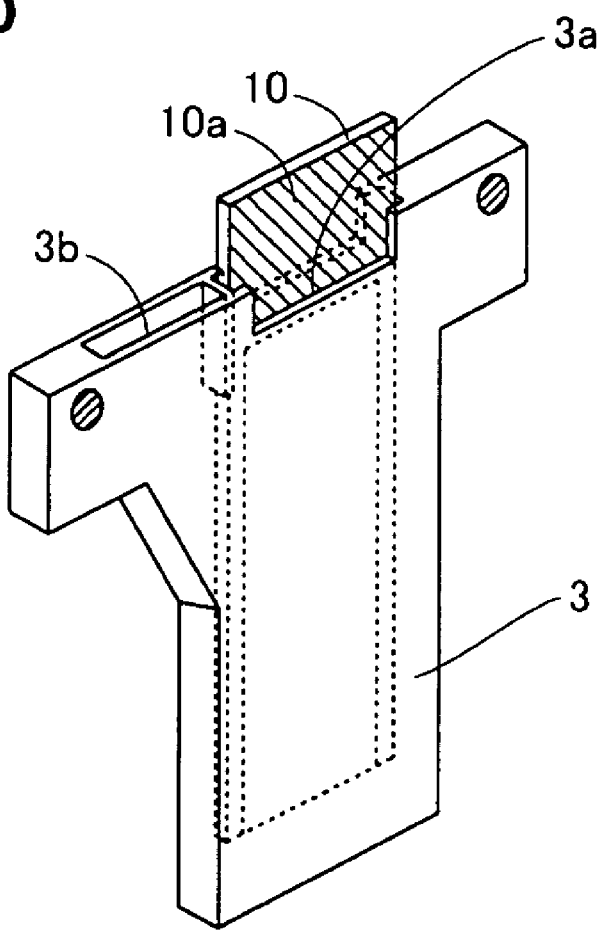

As shown in FIGS. 5 and 6, the resin cassette 3 is configured so as to be capable of accommodating a smeared slide glass 10 and a liquid (staining liquid) used in a staining process. Specifically, the cassette 3 includes a slide glass insertion hole 3a, and a stain sucking/dispensing hole 3b. Moreover, the slide glass insertion hole 3a and a stain sucking/dispensing hole 3b are internally connected.

As shown in FIG. 3, the cassette storage part 4 is provided for carrying the cassette 3, and includes a transport belt 4a.

As shown in FIG. 3, the first cassette transport part 5 is provided to transport a cassette 3 from the cassette storage part 4 to the slide glass insertion part 6 and staining part 7. The first cassette transport part 5 includes a cassette transport member 5a that is movable in the X direction, drive belt 5b for moving the cassette transport member 5a in the X direction, and a transport path 5c for transporting the cassette 3 supplied from the cassette storage part 4.

As shown in FIG. 3, the slide glass insertion part 6 is provided to insert the smeared and printed slide glass 10 in the slide glass insertion hole 3a of the cassette 3. The slide glass insertion part 6 includes a cassette turning part 6a to maintain a cassette 3 in a horizontal disposition for the insertion of a slide glass 10.

As shown in FIG. 3, the staining part 7 is provided to stain an unstained slide glass 10 by supplying a staining liquid to the stain sucking/dispensing hole 3b of the cassette 3 which has been transported by the cassette transport member 5a. The staining part 7 includes a feeding member 7a for feeding a cassette 3 that has been transported by the cassette transport member 5a to a second suction/discharge part 7d of the staining part 7, a transport belt 7b for transporting the cassette 3 fed from the feeding member 7a, first through fifth sucking/discharging parts 7c through 7g for supplying and discharging staining liquid to/from the cassette 3, and a fan 7h for drying the stained slide glass 10.

The second cassette transport part 8 is configured so as to be capable of transporting a cassette 3 which accommodates stained slide glass 10, to both an entrance 300a of the cassette supplying apparatus 300 and an entrance 9a (refer to FIG. 3) of the keeping part 9 of the blood smear slide preparing apparatus 100. The second cassette transport part 8 has a transport part 8b mounted on a frame 8a, drive belt 8c for moving the transport part 8b in the X direction, and a transport path 8d. The transport path 8d is provided so as to extend to a position at the entrance 300a of the cassette supplying apparatus 300. The transport path 8d forms a passage for the movement of the cassette 3 that is pushed by the transport path 8b.

As shown in FIG. 3, the keeping part 9 is provided to store the cassette 3, which contains the slide glass 10 that has been stained by the staining part 7. The sample on the stained slide glass 10 delivered to the keeping part 9 is visually analyzed. A feeding part 9b and transport belt 9c are provided in the keeping part 9. In the present embodiment, the feeding part 9b is mounted on the frame 8a of the second cassette transport part 8, and disposed in a region opposite the entrance 9a of the keeping part 9. The feeding part 9b is provided to move the cassette 3, which has been transported to the entrance 9a of the keeping part 9 by the second cassette transport part 8, to the keeping part 9 side.

In the present embodiment, a control part 110 of the blood smear slide preparing apparatus 100 has a function of controlling whether to transport a cassette 3 containing a stained slide glass 10 to the entrance 9a of the keeping part 9, or to the entrance 300a of the cassette supplying apparatus 300. The control part 110 controls the operation of the drive belt 8c that drives the transport part 8b of the second cassette transport part 8, and the operation of the feeding part 9b of the keeping part 9. The control part 110 is provided with a memory 111 for storing sample information such as the conditions under which the sample was prepared. The control part 110 is connected by a landline or wirelessly to the host computer 500 (refer to FIG. 2) so as to be capable of communication.

Figure 7:
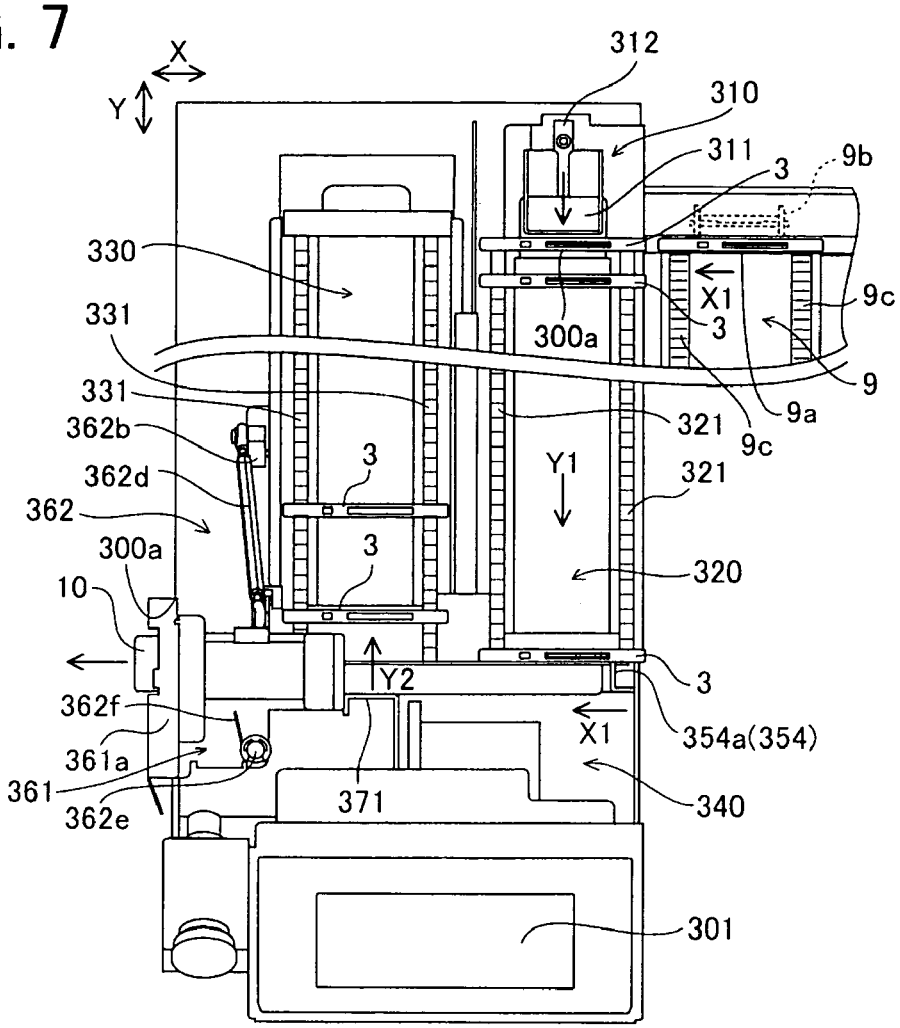
FIG. 7 is a top view of the cassette supplying apparatus of the embodiment of the slide preparing and image obtaining system of FIG. 1.

As shown in FIG. 7, the cassette supplying apparatus 300 is provided to transport a slide glass 10 contained in the cassette 3 received at the entrance 300a to the sample image obtaining apparatus 400 (refer to FIG. 1). As shown in FIG. 1, the cassette supplying apparatus 300 includes a display part 301, power switch 302, and cover 303. As shown in FIG. 7, the cassette supplying apparatus 300 is configured by a feeding part 310, cassette transport parts 320 and 330, and cassette turning part 340.

As shown in FIG. 7, the feeding part 310 is provided to move the cassette 3 that has arrived at the entrance 300a to the cassette transport part 320 side. The feeding part 310 is configured by a pushing member 311 for pushing a cassette 3 that has entered the entrance 300a, and a direct-drive guide 312 for moving the pushing member 311 in the arrow Y direction.

As shown in FIG. 7, the cassette transport part 320 is provided to transport a cassette 3, which has been pushed by the pushing member 311 of the feeding part 310, to the cassette turning part 340. The cassette transport part 320 has the function of storing the cassette 3, and is capable of storing approximately 100 individual cassettes 3. Furthermore, a cassette containing a smear slide with an urgent specimen (blood), or a cassette containing a smear slide prepared by manually by a technician or prepared by the blood smear preparing apparatus 100 of the present embodiment or a different sample preparing apparatus may be directly placed in the cassette transport part 320 from outside. A cassette 3 unrelated to a set sequence may also be placed in the cassette queue by introducing a cassette among the cassettes 3 transported from the blood smear slide preparing apparatus 100. As shown in FIG. 7, the cassette transport part 320 includes a pair of transport belts 321 for transporting a cassette 3 in the arrow Y1 direction.

Figure 8:
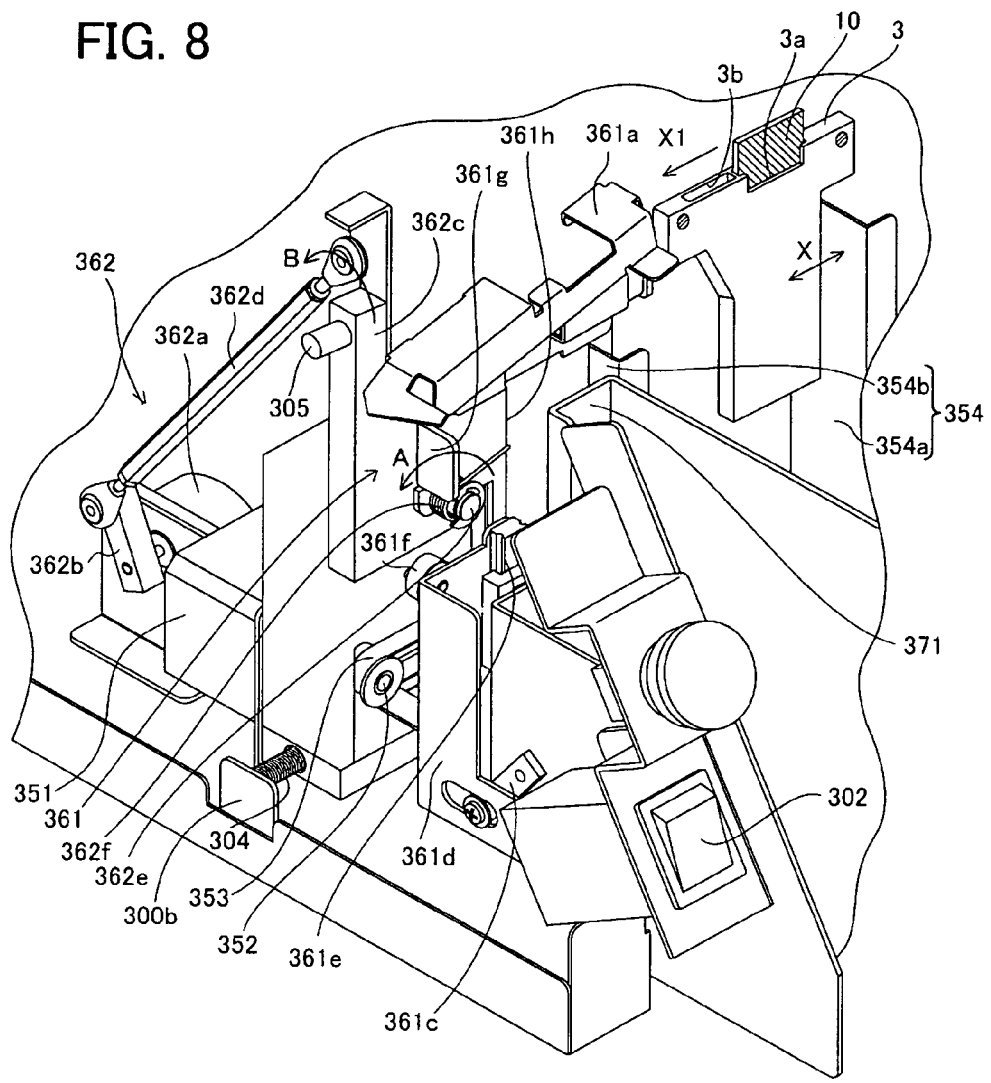
FIG. 8 is an enlarged perspective view of the cassette turning part of the cassette supplying apparatus of the embodiment of the slide preparing and image obtaining system of FIG. 1.
Figure 9:
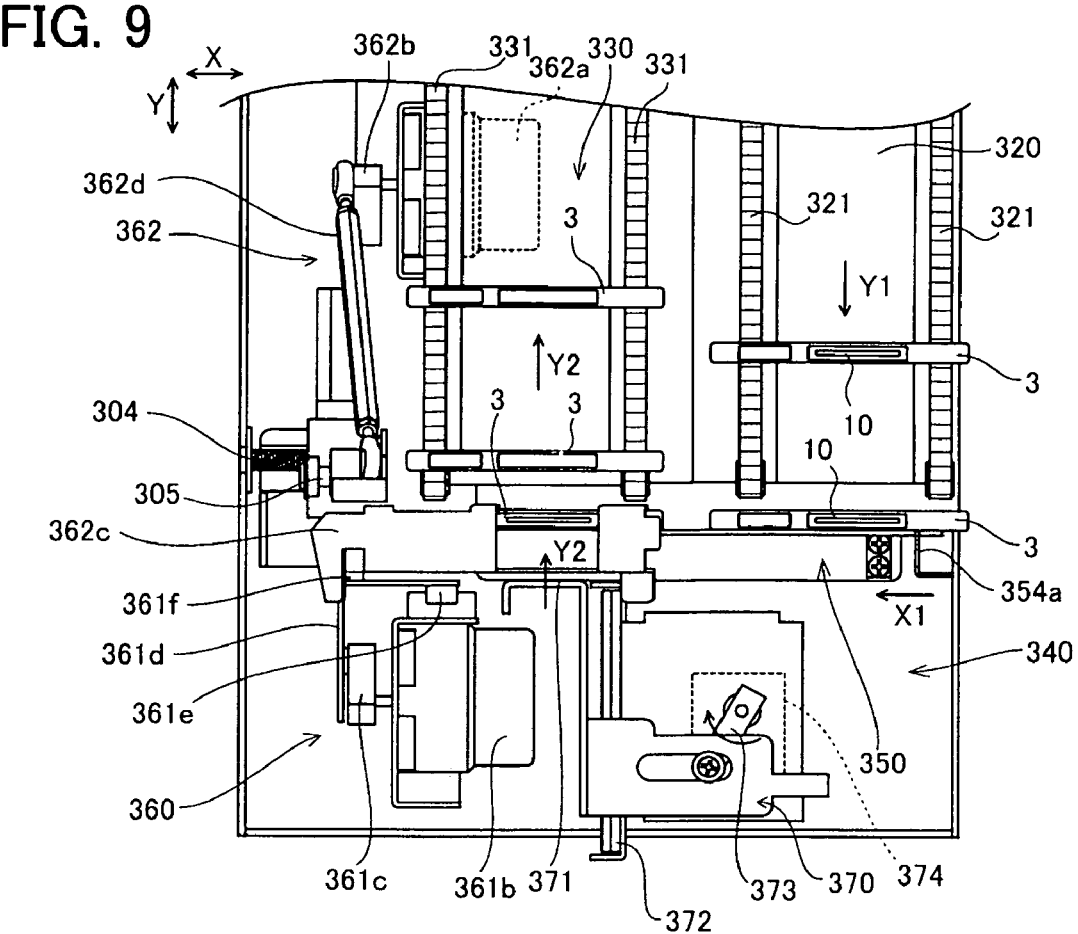
FIG. 9 is a top view of the cassette turning part of the cassette supplying apparatus of the embodiment of the slide preparing and image obtaining system of FIG. 1.

As shown in FIGS. 8 and 9, the cassette turning part 340 functions to arrange in a horizontal direction a cassette 3 that has been transported while disposed in a perpendicular direction. Thus, a slide glass 10 accommodated in a cassette 3 can be removed by a slide glass take-out part 410 (refer to FIG. 14; described later) of the sample image obtaining apparatus 400. The cassette turning part 340 is provided with a horizontal feeding part 350, turning part 360, and feeding part 370.

Figure 10:
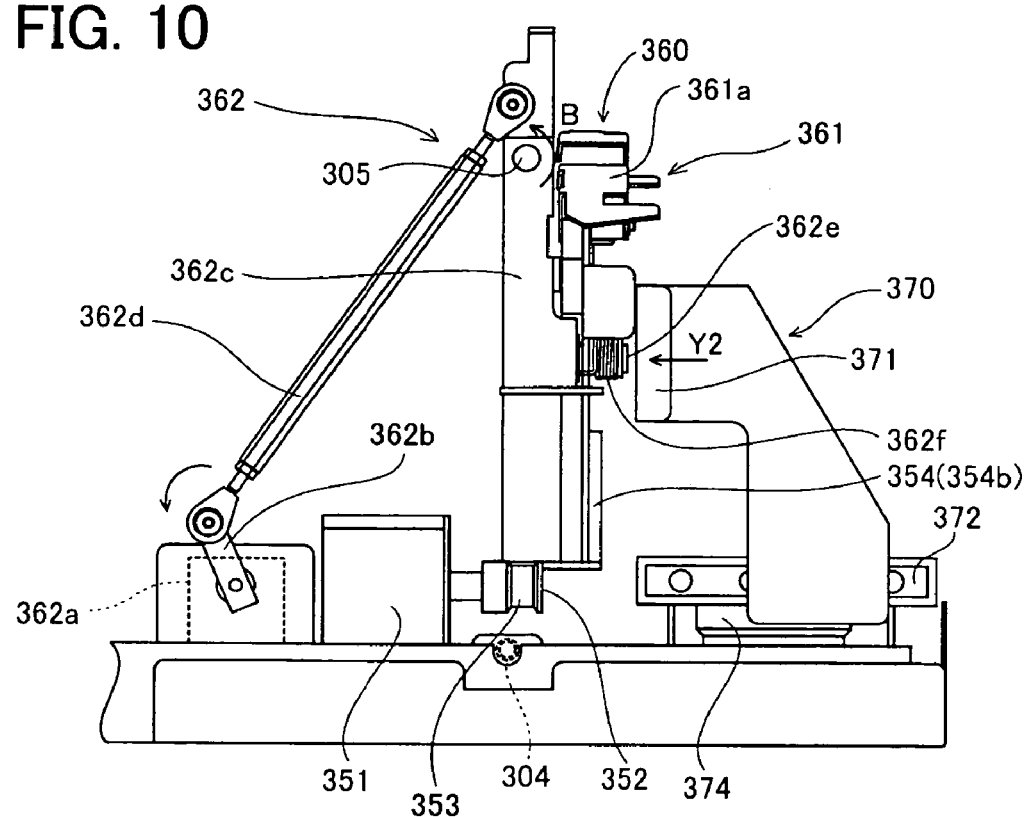
FIG. 10 is a side view of the cassette turning part of the cassette supplying apparatus of the embodiment of the slide preparing and image obtaining system of FIG. 1.

As shown in FIG. 10, the horizontal feeding part 350 is configured by a motor 351, pulley 352 connected to the motor 351, a pulley (not shown in the drawing) disposed a predetermined distance from the pulley 352, drive transmission belt 353, and moving member 354 coupled to the drive transmission belt 353. As shown in FIG. 8, the moving member 353 is provided with a cassette pushing part 354a for pushing the side end of a cassette 3 transported by the cassette transport part 320, and a pushing part 354b for pushing the turning part 360. Thus, the moving member 354', which is coupled to the drive transmission belt 353 and driven by the drive transmission belt 353, is moved in the X direction via the drive of the motor 351. As a result, a cassette 3 can be moved to the turning part 360 when the pushing part 354a pushes the side end of the cassette 3 that has been transported by the cassette transport part 320. Therefore, the entire turning part 360 is moved to the sample image obtaining apparatus 400 side (X direction) by the pushing part 354b pushing the turning part 360.

Figure 20:
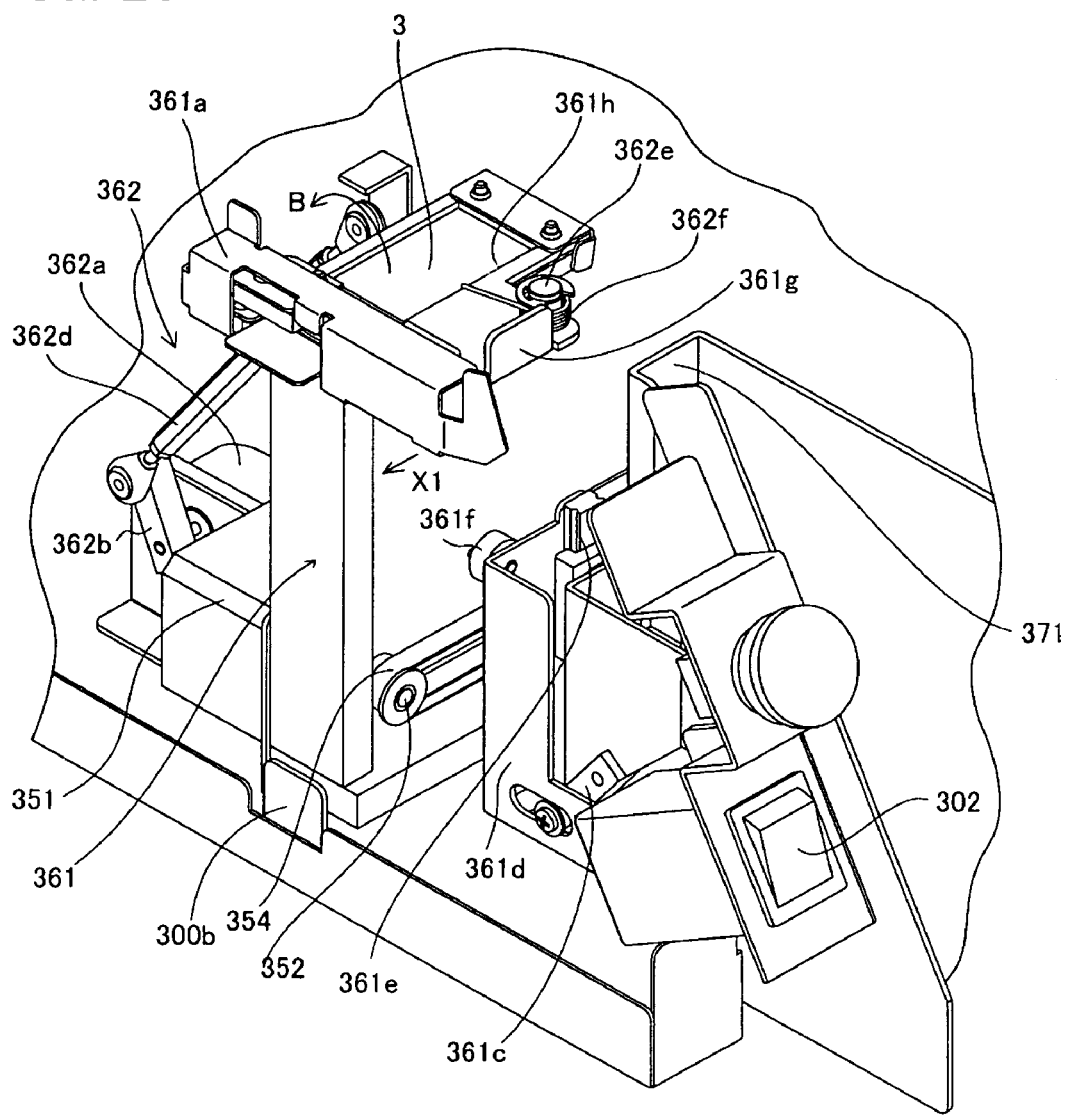

As shown in FIG. 8, the turning part 360 functions to turn the cassette 3 in the arrow B direction after the cassette 3 has been turned in the arrow A direction by the horizontal feeding part 350. That is, the cassette turning part 360 functions to arrange in a horizontal direction a slide glass 10 within the cassette 3 that has been transported while disposed in a perpendicular direction. As shown in FIGS. 8 and 20, the turning part 360 is movable in the X directions, and bends a spring 304 inserted on the shaft mounted on the chassis 300 via the pushing of the pushing part 354b of the horizontal feeding part 350. The turning part 360 includes a primary turning part 361 and a secondary turning part 362.

Figure 18:
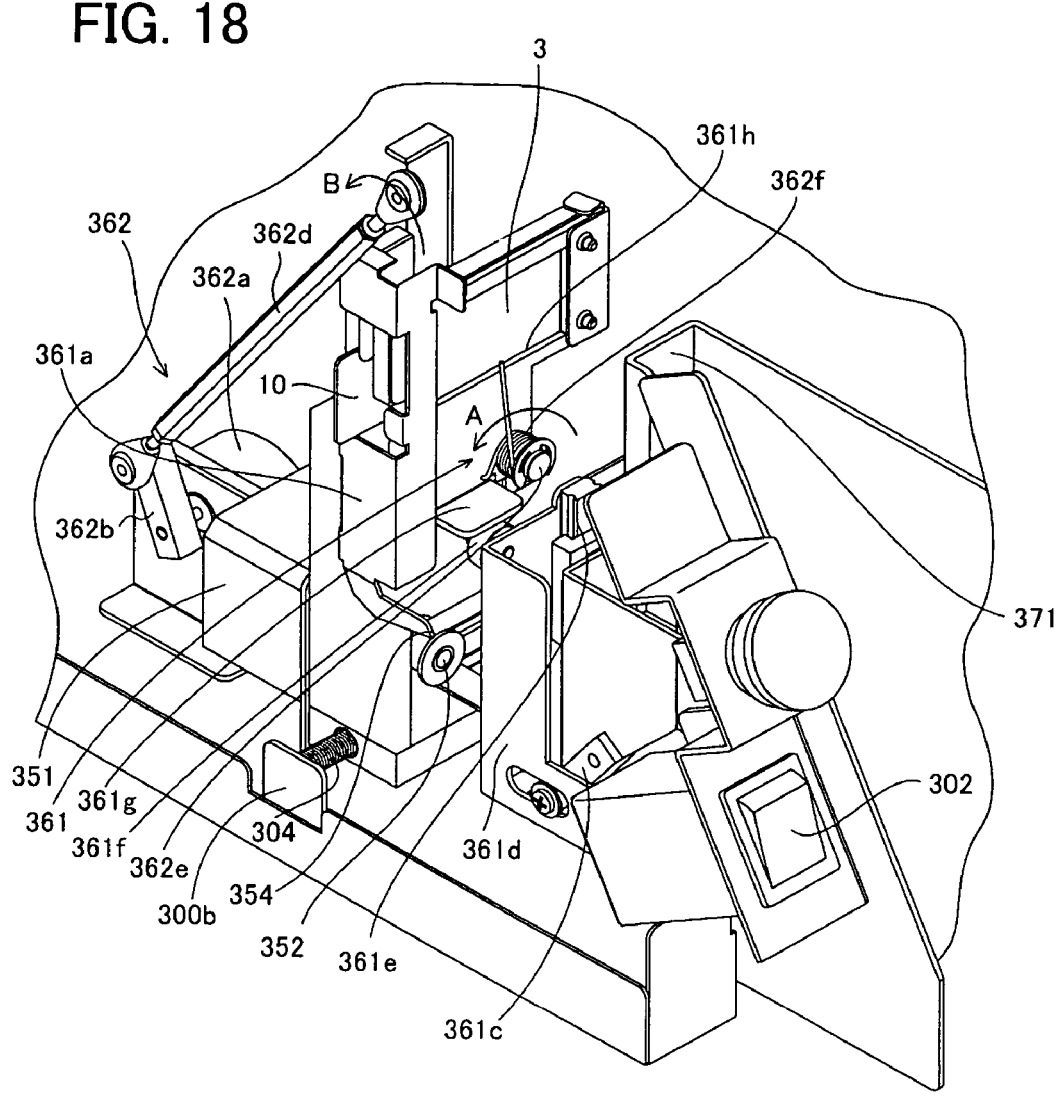
FIGS. 18 through 20 are perspective views illustrating the operation of the cassette turning part of the embodiment of the sample image obtaining system of FIG. 1.

The primary turning part 361 is provided to rotate the cassette 3 transported by the horizontal feeding part 350 in the arrow A direction to achieve a transverse orientation (refer to FIG. 18). As shown in FIGS. 8 and 9, the primary turning part 361 includes a cassette holding part 361a for accommodating the cassette 3, a motor 361b, arm 361c mounted on the shaft of the motor 361b, moving member 361d mounted on the arm 361c, direct-drive guide 361e for moving the moving part 361d in the Z direction, and pressure roller 361f mounted on the moving member 361d. The cassette holding part 361a is mounted on the shaft 362e so as to be rotatable, and the shaft 362e is mounted on the rotating member 362c of the secondary turning part 362 described later. The cassette holding part 361a is provided with a contact piece that contacts the pressure roller 361f mounted on the moving member 361d. The cassette holding part 361a is further provided with an opening 361h for inserting a pushing member 371 of the feeding part 370 described later.

Figure 19:
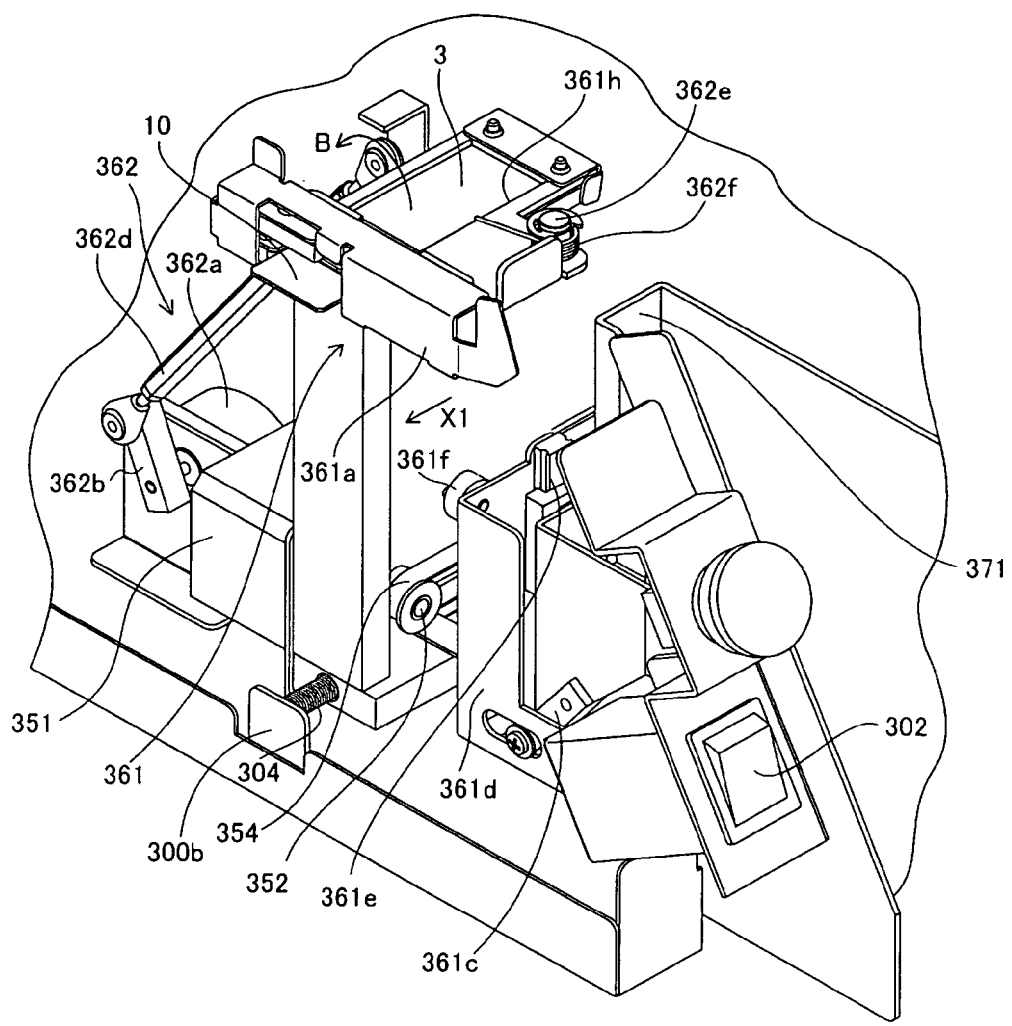

As shown in FIGS. 8 through 10, the secondary turning part 362 is provided to turn the cassette 3, which has been turned in the arrow A direction to a transverse orientation by the primary turning part 361 (refer to FIG. 18) in the arrow B direction to achieve a horizontal orientation (refer to FIG. 19). The secondary turning part 362 includes a motor 362a, an arm 362b mounted on the shaft of the motor 362a, a rotating member 362c mounted so as to be rotatable on the shaft 305 that is mounted on the chassis 300b, a link lever 362d one end of which is mounted on the arm 362b and the other end of which is mounted on the rotating member 362c, a shaft 362e mounted on the rotating member 362c, and a coil spring 362f mounted on the shaft 362e. The cassette holding member 361a of the primary rotating part 361 is mounted on the shaft 362e so as to be rotatable, and the shaft 362e is mounted on the rotating member 362c. The coil spring 362f mounted on the shaft 362e functions to exert a force to rotate the cassette holding member 361a in the arrow A direction. Thus, the cassette holding member 361a, which is rotatably mounted on the shaft 362e mounted on the rotating member 362c, is rotated in the arrow A direction (refer to FIG. 8) by the force exerted by the coil spring 362f so as to position the cassette 3 in a transverse orientation (refer to FIG. 18). From the condition shown in FIG. 18, the arm 362b is rotated by actuating the motor 362a of the secondary turning part 362, such that the rotating member 362c and the primary turning part 361 are rotated in the arrow B direction (refer to FIG. 8) via the link lever 362d. As a result, the cassette 3 attains a horizontal orientation (refer to FIG. 19).

The feeding part 370 is provided to move the cassette 3, from which the slide glass 10 has been removed by the slide glass take-out part 410 of the sample image obtaining apparatus 400 described later, to the cassette transport part 330 side. As shown in FIGS. 9 and 10, the feeding part 370 is configured by a pushing member 371, direct-drive guide 372 for moving the pushing member 371 in the Y2 direction, an arm 373, and motor 374. The pushing member 371 is mounted on the direct-drive guide 372. The direct-drive guide 372 extends along the Y direction. One end of the arm 373 is mounted on the pushing member 371 and the other end is coupled to the rotating shaft of the motor 374. Thus, one end of the arm 373 is turned via the drive of the actuation of the motor 374 so as to move the pushing member 371 along the direction in which the direct-drive guide 372 extends (Y direction).

The cassette transport part 330 has a configuration similar to that of the cassette transport part 320, and is provided to carry an empty cassette from which a slide glass 10 has been removed, and to store the empty cassette 3. As shown in FIG. 7, the cassette transport part 330 is capable of storing approximately 100 individual empty cassettes 3. The cassette transport part 330 includes a pair of transport belts 331 for transporting a cassette 3 in the arrow Y2 direction.

Figure 11:
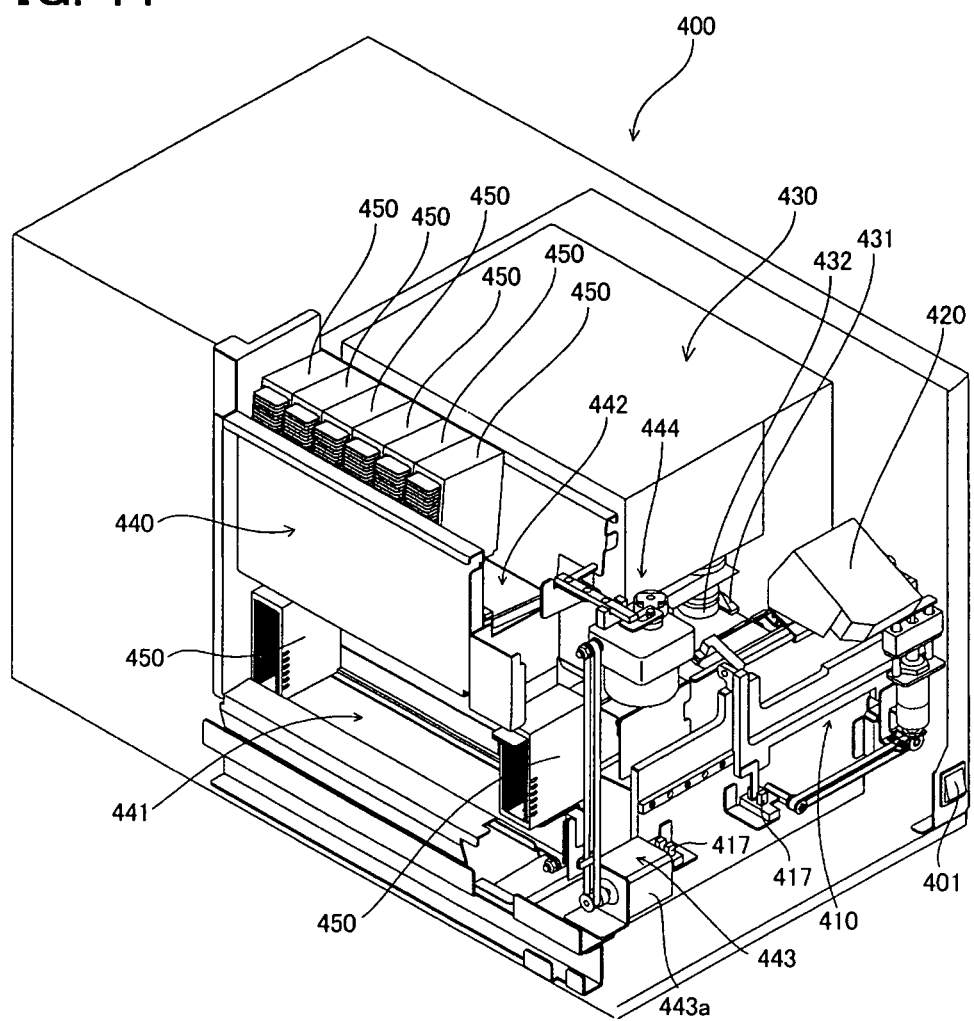
FIG. 11 is a perspective view of the sample image obtaining apparatus of the embodiment of the slide preparing and image obtaining system shown in FIG. 1.
Figure 12:
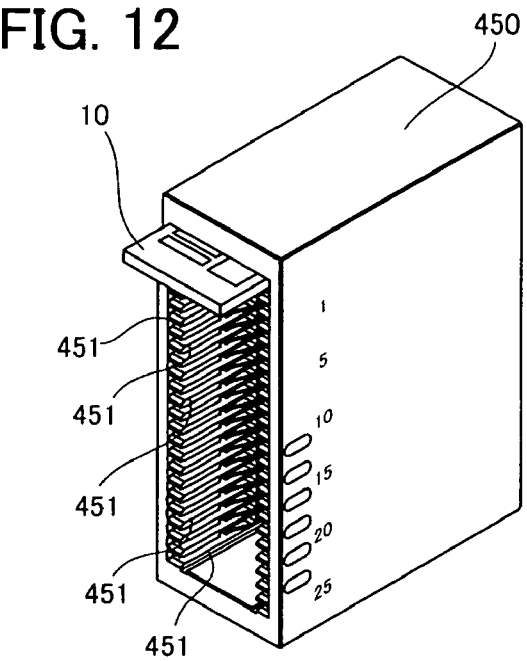
FIG. 12 is a perspective view of the magazine of the sample image obtaining apparatus of the embodiment of the slide preparing and image obtaining system shown in FIG. 1.

The sample image obtaining apparatus 400 has the function of obtaining images of the sample smeared in the sample smearing region 10f (refer to FIG. 4) of the received slide glass 10. The sample image obtaining apparatus 400 has the processing capability to obtain images of a sample smeared on 90 slide glasses 10 per hour. As shown in FIG. 1, the sample image obtaining apparatus 400 includes a power switch 401, a cover 402 that can open and close, and a door 403 provided on the side surface of the case so as to be openable and closable. A personal computer 404 is connected to the sample image obtaining apparatus 400. As shown in FIG. 2, the control part 404a of the personal computer (PC) 404 is connected to the host computer 500 via a landline or wirelessly so as to be capable of communication. As shown in FIG. 11, the sample image obtaining apparatus 400 is provided with a slide glass take-out part 410, barcode reading part 420, imaging part 430, magazine transport part 440, and magazine 450. As shown in FIG. 12, the magazine 450 has a capacity capable of accommodating 25 slide glasses 10. Numbers are affixed at positions on the side surface of the storage part 451 corresponding to the slide glasses number 1, 5, 10, 15, 20, and 25. The position of a predetermined slide glass 10 within the magazine 450 can be confirmed visually via these numbers.

Figure 13:
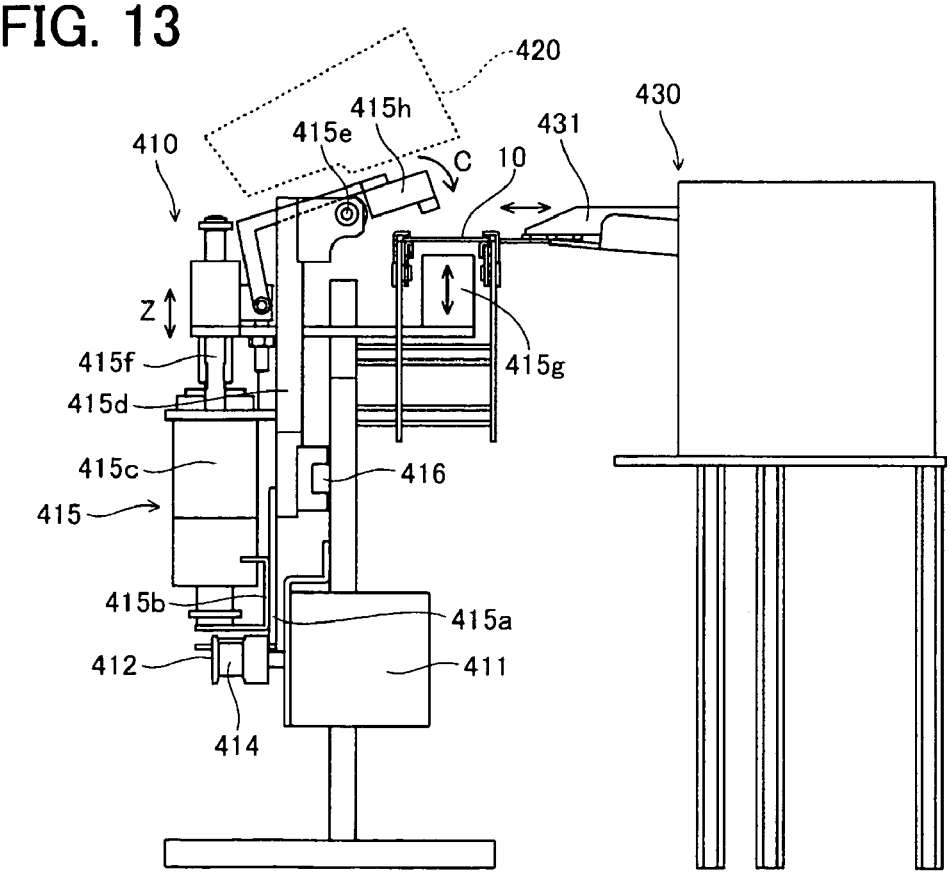
FIG. 13 is a side view of the sample image obtaining apparatus of the embodiment of the slide preparing and image obtaining system shown in FIG. 1.
Figure 14:
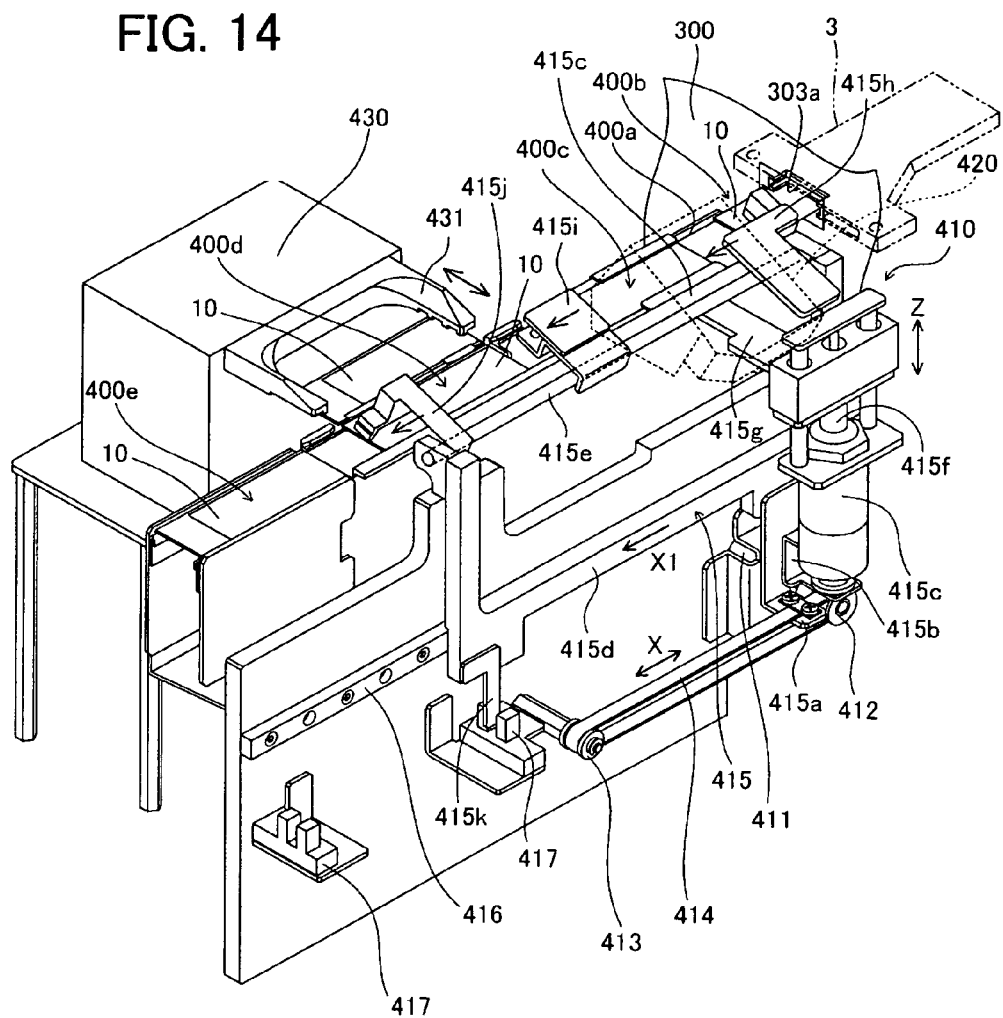
FIG. 14 is a perspective view of the sample image obtaining apparatus of the embodiment of the slide preparing and image obtaining system shown in FIG. 1.
Figure 15:
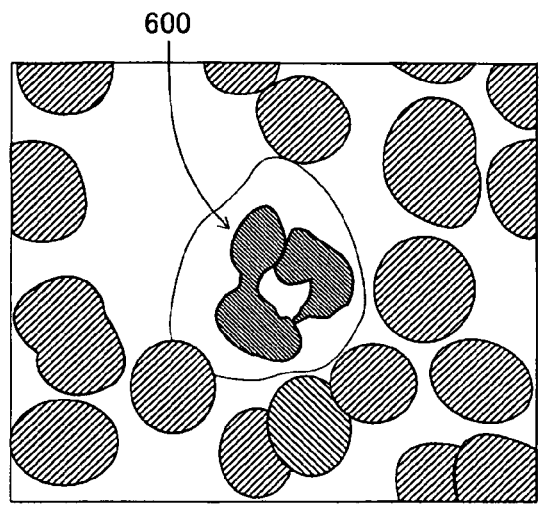
FIG. 15 is an image of a sample obtained by the imaging part of the sample image obtaining apparatus of the embodiment of the slide preparing and image obtaining system shown in FIG. 1.

As shown in FIGS. 13 and 14, the slide glass take-out part 410 has the function of taking out the a stained slide glass 10 from a cassette 3 that has been horizontally oriented by the cassette turning part 340 of the cassette supplying apparatus 300, and transporting the stained slide glass 10 to the barcode reading part 420. Moreover, the slide glass take-out part 410 functions to move the slide glass 10 in the X direction. The slide glass take-out part 410 is configured by a motor 411, pulley 412 connected to the motor 411, pulley 413 provided at a predetermined distance from the pulley 412, drive transmission belt 414 installed on pulley 412 and pulley 413, moving part 415 that moves in conjunction with the drive transmission belt 414, direct-drive guide (slide rail) 416 for moving the moving part 415 in the X direction, and two light shielding sensors 417. Thus, the drive transmission belt 414 is driven by the actuation of the motor 411 via the pulley 412, and the moving part 415 connected to the drive transmission belt 414 is moved in the X direction.

The moving part 415 is configured by a linkage 415a connected to the drive transmission belt 414, solenoid support 415b mounted on the linkage 415a, solenoid 415c supported by the solenoid support 415b, moving member 415d that is movable along a direct-drive guide (slide rail) 416 and mounted on the linkage 415a, support shaft 415e rotatably mounted on the moving part 415d, bottom chuck 415g that moves in vertical directions (Z directions) together with a rod 415f of the solenoid 415c, top chuck 415h which is mounted on the support shaft 415e and turns in the arrow C direction in linkage with the bottom chuck 415g, pressure parts 415i (refer to FIG. 14) and 415j (refer to FIG. 14) mounted on the support shaft 415e. Therefore, the bottom chuck 415g is moved in the Z direction by the rod 415f of the solenoid 415c and supports the bottom surface of a slide glass 10 in the transport path 400a. At this time, the top chuck 415h is turned in the arrow C direction together with the support shaft 415e in linkage with the movement of the bottom chuck 415g in the Z direction (upward direction). The bottom surface of the slide glass 10 is supported in the transport path 400a. Thus, the slide glass 10 is held between the bottom chuck 415g and the top chuck 415h in the transport path 400a. Since the pressure parts 415i and 415j are mounted on the support shaft 415e, the pressure parts 415i (refer to FIG. 14) and 415j (refer to FIG. 14) turn in the arrow C direction in linkage with the turning of the top chuck 415h in the arrow C direction. As shown in FIG. 14, a detection piece 415k is provided on the moving member 415d to block the light of the two light shielding sensors 417, such that the position of the moving part 415 can be detected by the two light shielding sensors 417.

The top chuck 415h and the bottom chuck 415g have the functions of holding a slide glass 10 disposed at the entrance position 400b in the transport path 400a by the cassette turning part 340 of the cassette supplying apparatus 400, and transporting the slide glass 10 in the X1 direction to the reading position 400c of the barcode reading part 420. The pressure part 415i has the function of transporting a slide glass 10 in the transport path 400a by the top chuck 415h and bottom chuck 415g to a feed position 400d from which the slide glass 10 can be pulled out by the slide chuck 431 of the imaging part 430. The pressure part 415j has the function of transporting the slide glass 10 disposed at the feed position 400d in the transport path 400a to the magazine entrance position 400e in the transport path 400a.

In the present embodiment, the barcode reading part 420 is a two-dimensional barcode reader as shown in FIG. 11, and has the function of reading a two-dimensional barcode 10b (refer to FIG. 4) printed on the frosted region 10a of the slide glass 10. After the two-dimensional barcode 10b has been read, the bottom end of the slide glass 10 is pushed by the pushing part 415i to transport the slide glass 10 to the feed position 400d where it can be grabbed by the slide chuck 431 of the imaging part 430.

Figure 16:
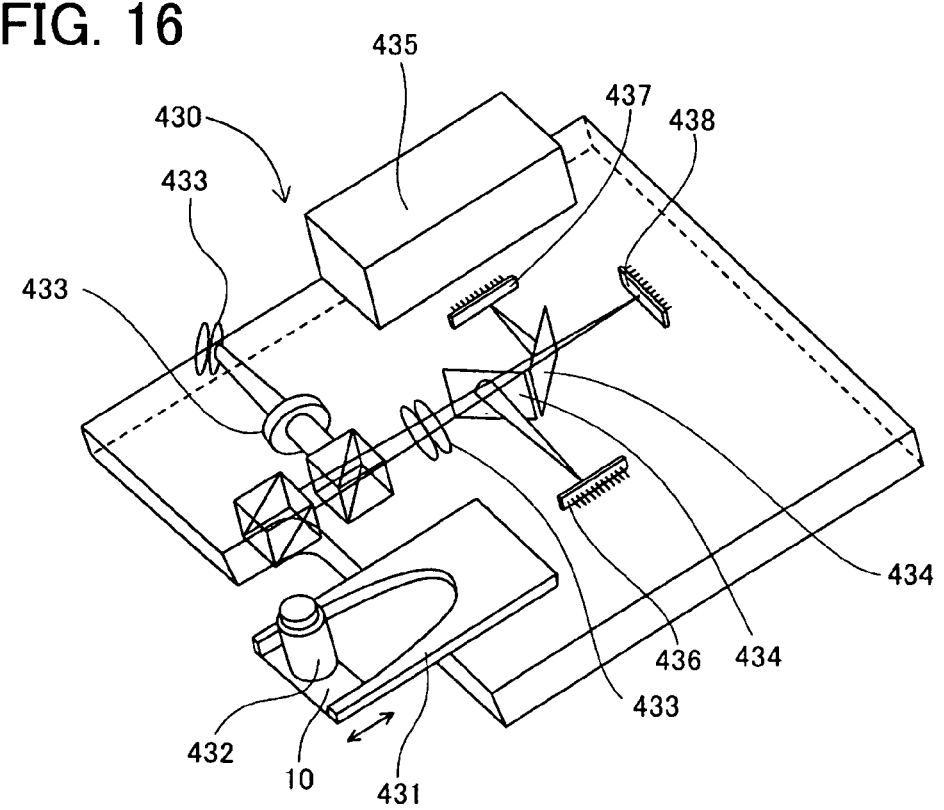
FIG. 16 is a schematic view of the imaging part of the sample image obtaining apparatus of the embodiment of the slide preparing and image obtaining system shown in FIG. 1.

As shown in FIG. 16, the imaging part 430 is provided to obtain an image of the sample (refer to FIG. 15) smeared in the sample smearing region 10f (refer to FIG. 4) of the slide glass 10. The imaging part 430 includes a slide chuck 431, objective lens 432, a plurality of lenses 433, half mirror 434, CCD camera 435, and line sensors 436 through 438. The slide chuck 431 has the function of moving forward and gripping the slide 10 which has been transported to the feed position 400d in the transport path 400a, and thereafter moving downward and disposing the slide glass 10 at a position below the objective lens 432. Thus, the image of the sample in the sample smear region 10f the slide glass 10 positioned below the objective lens 432 is obtained by the CCD camera 435 through the plurality of lenses 433. The line sensor 436 has the function of detecting white blood cells 600 (refer to FIG. 15 distinctively stained blue. The line sensors 437 and 438 are used to adjust the focus of the CCD camera 435.

Figure 17:
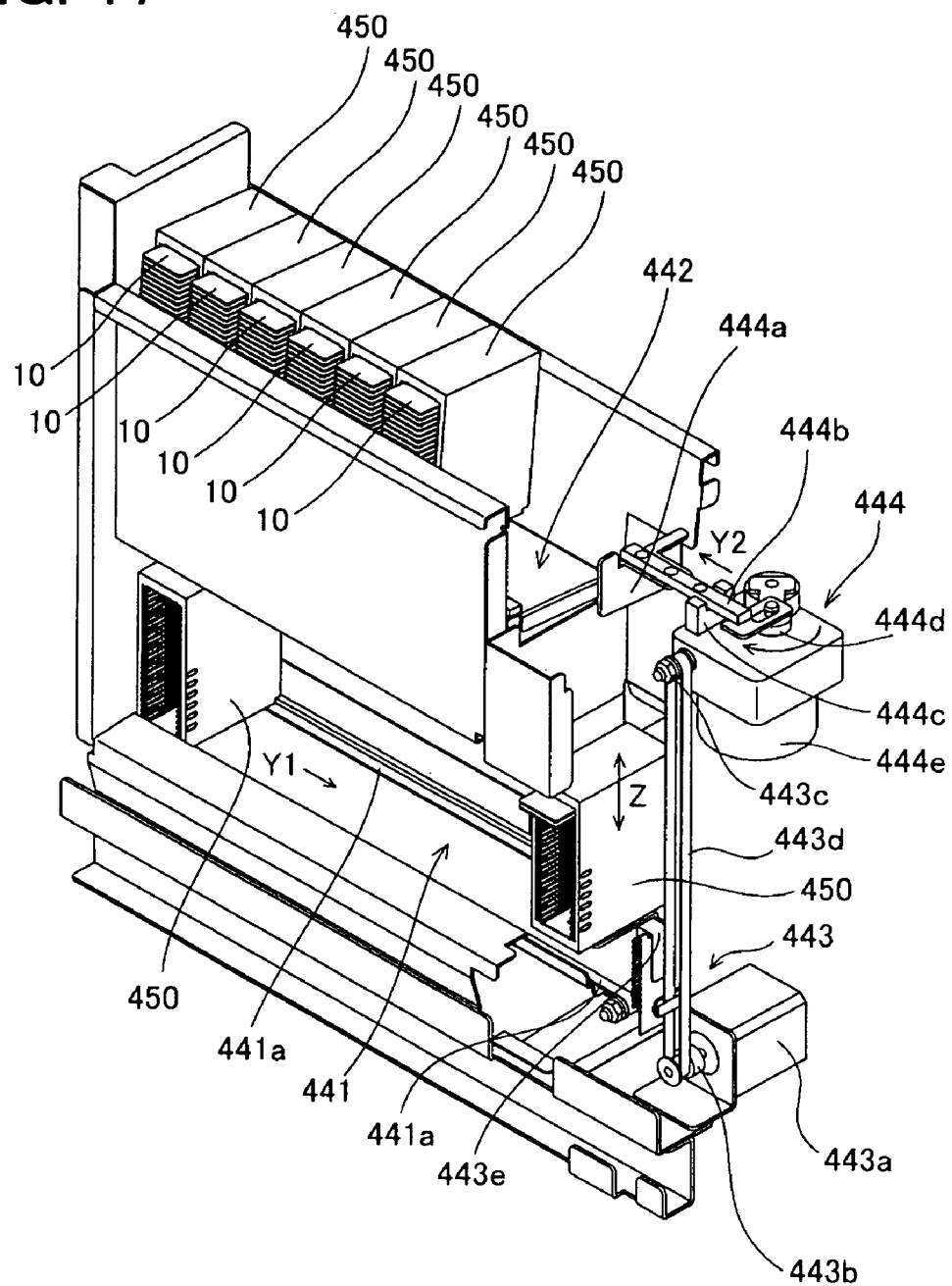
FIG. 17 is a perspective view of the magazine transport part of the sample image obtaining apparatus of the embodiment of the slide preparing and image obtaining system shown in FIG. 1.

As shown in FIG. 17, the magazine transport part 440 is configured by a magazine storage part 441 and magazine storage part 442, magazine transport part 443, and magazine feeding part 444. The magazine transport part 440 has the function of transporting an empty magazine 450, which has been supplied by opening the door 403 (refer to FIG. 1) provided in the side surface of the casing so as to be openable, from the magazine storage part 441 to the magazine storage part 442.

In the present embodiment, the magazine storage part 441 is provided to store a plurality of empty magazines 450 as shown in FIG. 17. The magazine storage part 441 includes a pair of transport belts 441a to transport the magazine 450 in the Y1 direction. The magazine storage part 442 is provided to store a plurality of magazines 450 that contain slide glass 10. The magazine storage parts 441 and 442 respectively accommodate a maximum of eight individual magazines 450.

The magazine transport part 443 is configured so as to transport an empty magazine 450 from the lower magazine storage part 441 to the upper magazine storage part 442. The magazine transport part 443 includes a motor 443a, pulley 443b connected to the shaft of the motor 443a, pulley 443c disposed above the pulley 443b at a predetermined distance, drive transmission belt 443d installed on the pulley 443b and 443c, and transport member 443e coupled to the drive transmission belt 443d. Thus, the drive transmission belt 443d is driven via the actuation of the motor 443a through the pulley 443b. As a result, the transport member 443e coupled to the drive transmission belt 443d is moved in the Z direction. Thus, the transport member 443e holding a magazine 450 can be moved in the Z direction.

The magazine feeding part 444 has the function of delivering the magazine 450, which contains a slide glass 10 and was transported upward by the magazine transport part 443, to the magazine storage part 442. The magazine feeding part 444 is configured by a pushing member 444a, movable slide rail 444b, slide rail support member 444c that movably supports the slide rail 444b, arm 444d, and a motor 444e. The pushing member 444a is mounted on the slide rail 444b. The slide rail 444b extends along the Y direction. One end of the arm 444d is mounted on the slide rail 444b through a slot, and the other end is coupled to the rotating shaft of the motor 444e. Thus, one end of the arm 444d is turned via the actuation of the motor 444e, and the side rail 444b is moved in the Y direction relative to the slide rail support member 444c. In this way the pushing member 444a is moved in the Y direction. Therefore, a magazine, which has been transported upward by the magazine transport part 443, is pushed by the pushing part 444a and is pushed to the magazine storage part 442 side.

The personal computer (PC) 404 has the functions of performing digital image processing of the image obtained from the stained slide glass 10, and automatically analyzing the blood cells, as shown in FIGS. 1 and 2. The personal computer 404 has a control part 404a, display part 404b, and input part 404c. The control part 404a has the functions of controlling the operation of the imaging part 430 and slide glass take-out part 410, and analyzing the sample based on the image of the sample obtained by the imaging part 430 (refer to FIG. 15). The control part 404a is provided with a memory 404d (refer to FIG. 2) for storing the identification information (two-dimensional barcode 10b) obtained by the barcode reading part 420 and the image of the sample obtained by the imaging part 430 corresponding to the identification information. The memory 404d has the function of storing the identification information (two-dimensional barcode 10b) obtained by the barcode reading part 420 and the position of the slide glass 10 within the magazine 450 corresponding to the identification information.

The operation of the sample image obtaining system of the present embodiment is described below with reference to FIGS. 1 through 20.

First, when performing a sucking/dispensing operation by the blood smear slide preparing apparatus 100, the start switch 102 is pressed to start the blood smear slide preparing apparatus 100, as shown in FIG. 1. In this state, a sample rack 150 accommodating test tube 151 containing a blood sample is placed in the rack transporting apparatus 200. Then, an automatic sucking start switch displayed on the display operating part 101 is pressed. Thus, the sample rack 150 is transported to a position accessible to the hand member 160 of the blood smear slide preparing apparatus 100, and the test tube 150 containing the blood is grabbed by the hand member 160. The test tube 151 is lifted by raising the hand member 160. The blood contained in the test tube 151 is stirred by turning the hand member 160, and thereafter the test tube 151 is disposed in the sucking/dispensing part 1 as shown in FIG. 3. The piercer 1a pierces the rubber stopper 151a of the test tube 151 and suctions the blood. During the suction operation, the valve 1d is opened (ON) and the valve 1e is closed (OFF). After the suction operation is completed, the valve 1d is closed (OFF) and the valve 1e is opened (ON). Thereafter, the pipette 1b is moved to the dispensing/smearing position shown in FIG. 3.

Next, a cassette 3 delivery operation is performed by the cassette storage part 4 as shown in FIG. 3 in parallel with the sucking/dispensing operation. Specifically, a cassette 3 is first placed in the cassette storage part 4. Thus, a cassette 3 is transported by the feed belt 4a of the cassette storage part 4 and thereafter disposed in the transport path 5c.

Then, the control part 110 of the blood smear slide preparing apparatus 100 obtains sample information from the host computer 500 (refer to FIG. 2). The sample information includes information such as the specimen number of the sample smeared on the slide glass 10, and number of prepared smear slides. The sample information includes information regarding whether slides are prepared as visual smear slides or automatic analysis smear slides, or whether smear slides are prepared as both visual smear slides and automatic analysis smear slides. The sample information also includes information such as whether or not analysis is to be performed by the sample image obtaining apparatus 400. Then, the smearing conditions are recalled from a database stored in the control part 110 based on the obtained sample information. The smearing conditions are set beforehand for the preparation of smear slides. For example, the amount of blood to be used, the angle of the drawing glass, moving speed of the drawing glass and the like, are set in accordance with smeared sample that is desired. Thereafter, blood is dripped (dispensed) on the slide glass 10 using a pipette 1b based on the recalled smearing conditions. When preparing smear slides for automatic analysis and smear slides for visual inspection, the same blood is dispensed to each of two slide glasses 10. Then, when preparing the smear slide for automatic analysis, blood is dispensed in an amount corresponding to an automatic analysis smear slide. Then, when preparing the smear slide for visual inspection, blood is dispensed in an amount corresponding to a visual analysis smear slide.

Next, the smearing operation is performed by the smearing part 2 based on the smearing conditions. The smearing operation performed by the smearing part 2 is performed in parallel with the sucking/dispensing operation or after the sucking/dispensing operation by the sucking/dispensing part 1. The smearing part 2 supplies a slide glass 10 to the smearing/dispensing position 20, as shown in FIG. 3. Blood dripped on the slide glass 10 is smeared and dried, and information is printed on the slide glass 10. Specifically, slide glasses 10, which are held in two slide glass holding parts 2b of the slide glass supplying part 2a, are supplied onto a transport belt 2e via removing part not shown in the drawing and the transport belts 2d and 2e. The transport belt 2e transports the slide glass 10 to the dispensing/smearing position 20. The operation of transporting the slide glass 10 to the dispensing/smearing position 20 is accomplished before the sucking/dispensing operation. In this state, blood is dripped (dispensed) onto the slide glass 10 using the pipette 1b.

Thereafter, the drawing glass 2c is moved so as to abut the slide glass 10, and the blood dripped on the slide glass 10 at the dispensing/smearing position 20 is smeared by reciprocally moving the drawing glass 2c in the lengthwise direction of the slide glass 10. The contact angle of the drawing glass 2c on the slide glass 10 and the speed of the reciprocating movement of the drawing glass 2c are adjusted when preparing a smear slide for automatic analysis and when preparing a smear slide for visual inspection at this time. Specifically, this adjustment entails ensuring that the thickness of the sample to be used for automatic analysis is less than the thickness of the sample to be used for visual inspection. Thereafter, the smeared slide glass 10 is transported to the drying position 21a by the transport belt 2e. At the drying position 21a, the blood smeared on the slide glass 10 is dried with cool air by the fan 2f. The cool air drying of the slide glass 10 is performed twice at two adjacent drying positions 21a and 21b. Subsequently, the smeared slide glass 10 is moved to the printing part 2g by the slide glass transport part 2h. At the printing part 2g, a two-dimensional barcode 10b containing sample information such as sample number, date, reception date, patient name and the like, and three lines of text data including the date, kanji characters for patient name and the like, are printed in the frosted region 10a of the slide glass 10, as shown in FIG. 4.

Next, cassettes 3 (refer to FIGS. 3 and 6) disposed in the transport path 5c are transported one by one to the slide glass insertion part 6 via the cassette transport part 5. That is, the cassette transport member 5a of the cassette transport part 5 pushes and moves the side surface of the cassette 3 such that the cassette 3 is transported to the slide glass insertion part 6.

Then, the smeared slide glass 10 is inserted in the cassette 3. Thereafter, the slide glass 10 is transported to the staining part 7 by the cassette transport member 5a and subjected to the staining process.

Specifically, the cassette 3 is moved from the perpendicular position to a horizontal position (refer to the position indicated by the dashed line in FIG. 3) by turning the cassette turning part 6a in a predetermined direction. Thus, the cassette 3 is placed so that the slide glass 10 can be inserted. In this state, the vertical moving piece 2j of the smearing part 2 is advanced and the smeared slide glass 10 is inserted into the slide glass insertion hole 3a of the cassette 3. In this way the smeared slide 10 is inserted in the cassette 3. Subsequently, the cassette 3 is returned to the original perpendicular position by turning the cassette turning part 6a in the opposite direction to the previously mentioned predetermined direction. In the staining part 7, the smeared slide glass 10 is first lifted from the slide glass insertion hole 3a of the cassette 3 by the first sucking/discharging part 7c, and methanol is dispensed to the stain sucking/dispensing hole 3b of the cassette 3. After the smeared slide glass 10 has been returned to the cassette 3, the cassette 3 holding the smeared slide glass 10 is set one at a time on the transport belt 7b by the feeding member 7a. Then, the cassette 3 is transported to the second sucking/dispensing part 7d by the transport belt 7b.

In the second sucking/discharge part 7d, the smeared slide glass 10 is first lifted from the slide glass insertion hole 3a of the cassette 3. Then, the smeared blood on the slide glass 10 is dried by evaporating the moisture content on the slide surface via an air flow from the fan 7h directed to the sample smearing region of the slide glass 10 for approximately 1 to 60 seconds. Approximately 20 to 120 seconds elapses during the time the smeared slide glass 10 is immersed in the methanol by the first sucking/discharge part 7c until the slide glass 10 is lifted by the second sucking/discharge part 7d (immersion time).

The staining process (May-Grunwald/Giemsa double staining) is performed next. In the second sucking/discharge part 7d, after the methanol is suctioned from the stain sucking/dispensing hole 3b of the cassette 3, the slide glass 10 is returned to the slide glass insertion hole 3a of the cassette 3. Then, May-Grunwald stain (99% methanol) is dispensed from the stain sucking/dispensing hole 3b of the cassette 3, and the smeared slide glass 10 is immersed in the May-Grunwald stain. Thus, the May-Grunwald/Giemsa double staining process is started. The smeared slide glass 10 is subjected to the staining process, immersion in the May-Grunwald stain, for approximately 1 to 5 minutes while the cassette 3 is transported by the transport belt 7b. After the May-Grunwald stain has been discharged from the stain sucking/dispensing hole 3b of the cassette 3 by the third sucking/discharge part 7e, diluted May-Grunwald stain is dispensed to the stain sucking/dispensing hole 3b of the cassette 3. The smeared slide glass 10 is immersed in the diluted May-Grunwald stain, for approximately 1 to 5 minutes while the cassette 3 is transported by the transport belt 7b. After the diluted May-Grunwald stain has been discharged from the stain sucking/dispensing hole 3b of the cassette 3 by the fourth sucking/discharge part 7f, diluted Giemsa stain is dispensed to the stain sucking/dispensing hole 3b of the cassette 3. The smeared slide glass 10 is immersed in the diluted Giemsa stain, for approximately 1 to 20 minutes while the cassette 3 is transported by the transport belt 7b.

After the diluted Giemsa stain has been discharged from the stain sucking/dispensing hole 3b of the cassette 3 by the fifth sucking/discharge part 7g, washing solution is dispensed to the stain sucking/dispensing hole 3b of the cassette 3 and the stained slide glass 10 is rinsed. Thereafter, the stained slide glass 10 is dried by the fan 7h.

In the present embodiment, the control part 110 determines the transport destination of a cassette 3 holding a stained slide glass 10 transported by the transport belt 7b of the staining part 7 based on the sample information. That is, the control part 110 determines whether the cassette 3 should be transported to the entrance 9a (refer to FIG. 7) of the keeping part 9 of the blood smear slide preparing apparatus 100 or the entrance 300a (refer to FIG. 7) of the cassette supplying apparatus 300.

The cassette 3 holding the stained slide glass 10 is transported to the determined destination by the second cassette transport part 8 based on the transport destination information determined by the control part 110. Then, the cassette 3, which holds the stained slide glass 10 transported to the entrance 9a of the keeping part 9 of the blood smear slide preparing apparatus 100, is moved to the keeping part 9 side by the transport part 9b of the keeping part 9.

On the other hand, a cassette 3, which holds a stained slide glass 10 transported to the entrance 300a of the cassette supplying apparatus 300, is pushed to the cassette transport part 320 side by the feeding part 310, and is stored in the cassette transport part 320. Then, the cassette 3 is transported to the turning part 340 by the transport belt 321 of the cassette transport part 320.

The cassette 3 transported to the cassette turning part 340 is transported in the X1 direction by the transverse feeding part 350 of the cassette turning part 340, as shown in FIGS. 8 and 9. Specifically, the moving member 354, which is coupled to the drive transmission belt 353 and driven by the drive transmission belt 353, is moved in the X1 direction via the drive of the motor 351 and the pulley 352. At this time, a side end of the cassette 3 transported by the cassette transport part 320 is pushed by the cassette pushing part 354a such that the cassette 3 is transported to the turning part 360 side so as to be held by the cassette holding member 361a of the cassette turning part 360.

The cassette 3 held by the cassette holding member 361a of the turning part 360, is turned in the arrow A direction by the first turning part 361, as shown in FIG. 18. Specifically, the arm 361c is turned by the motor 361b, and the moving member 361d is moved in the Z direction (downward). At this time, the cassette holding member 361a is forced in the arrow A direction by the coil spring 362f mounted on the shaft 362e of the second turning part 362. Therefore, the cassette holding part 361a is turned in the arrow A direction on the shaft 362e while supported by the pressure roller 361f of the moving member 361d.

As shown in FIG. 19, the first turning part 361 and the cassette 3 that has been turned in the arrow A direction (refer to FIG. 18) by the first turning part 361 are turned in the arrow B direction by the second turning part 362 such that the cassette 3 and the slide glass 10 within the cassette 3 are disposed in a horizontal direction. Specifically, the arm 362b is turned by the actuation of the motor 362a, and the turning member 362c and the first turning part 361 are turned in the arrow B direction on the shaft 305 (refer to FIG. 8) via the link lever 362d.

As shown in FIG. 20, when the second turning part 362 has been turned in the arrow B direction (refer to FIG. 19), the transverse feeding part 350 is turned in the X1 direction to move the turning part 340, which includes the first turning part 361 and second turning part 362, in the X1 direction. That is, the cassette turning part 340 is moved in the X1 direction while the spring on the shaft is contracted by the transverse feeding part 350 moving in the X1 direction. Thus, the slide glass 10 protrudes from the opening 303a (refer to FIGS. 1 and 7) provided in the side surface of the cover 303, and is fed to the entrance position 400b where the slide glass 10 is accessible to the top chuck 415h and bottom chuck 415g of the slide glass take-out part 410 of the sample image obtaining apparatus 400 as shown in FIG. 13.

The cassette 3, from which the slide glass 10 has been removed by the top chuck 415h and bottom chuck 415g of the slide glass take-out part 410 of the sample image obtaining apparatus 400, is re-disposed from the horizontal orientation (refer to FIG. 20) to a perpendicular orientation (refer to FIG. 8) by reversing the operation of the previously described operation by the first turning part 361 and second turning part 362. The perpendicularly oriented empty cassette 3 is pushed to the cassette transport part 330 side (arrow Y2 direction) by the pushing member 371 of the feeding part 370, and is stored in the cassette transport part 330, as shown in FIGS. 9 and 10. The empty cassettes 3 are sequentially loaded by transporting the cassette transport part 330 in the Y direction via the transport belt 331.

Then, the stained slide glass 10, which has been moved to the entrance position where it is accessible to the top chuck 415h and bottom chuck 415g of the slide glass take-out part 410 of the sample image obtaining apparatus 400, is removed from the cassette 3 in the slide glass take-out part 410, as shown in FIG. 14. The stained slide glass 10 is transported to the reading position of the barcode reading part 420. Specifically, the bottom chuck 415g is moved in the Z direction by extension in the Z direction of the rod 415f of the solenoid 415c and supports the bottom surface of a slide glass 10 in the transport path 400a. At this time, the top chuck 415h is turned in the arrow C direction together with the support shaft 415e in linkage with the movement of the bottom chuck 415g in the Z direction (upward direction), and supports the bottom surface of the slide glass 10 in the transport path 400a. Thus, the slide glass 10 is held by the bottom chuck 415g and the top chuck 415h in the transport path 400a. When the slide glass 10 is gripped by the top and bottom chucks, the pulley 412 and drive transmission belt 414 are driven by the actuation of the motor 411, and the moving part 415 is moved in the X1 direction in linkage with the drive transmission belt 414. In this way the slide glass 10 gripped by the top chuck 415h and the bottom chuck 415g is transported to the reading position 400c.

The barcode reading part 420 reads the two-dimensional barcode 10b printed on the frosted region 10a of the slide glass 10 as shown in FIG. 11. Then, the specimen number of the stained slide glass 10 read by the barcode reading part 420 is sent to the control part 404a of the personal computer 400. Accordingly, the two-dimensional barcode 10b of the slide glass 10 can be read at a position directly before imaging by the imaging part 430. Thereafter, the stained slide glass 10, which has been read by the barcode reading part 420, is pushed by the pressure part 415i of the slide glass take-out part 410 and moved in the X1 direction along the transport path 400a. In this way the stained slide glass 10 is transported to the feed position 400d at which it is accessible to the slide chuck 431.

As shown in FIG. 16, after the slide glass 10 disposed at the feed position 400d has been gripped by the slide chuck 431 that has been moved forward, the slide chuck 431 is moved backward and drawn into the imaging part 430. In this way the slide glass 10 is positioned below the objective lens 432. An image of the sample on the slide glass 10 gripped by the slide chuck 431 is obtained by the CCD camera 435 of the imaging part 430 through the plurality of lenses 433 and the half mirror 434. Thus, a plurality of images are obtained from the sample of the slide glass 10 (refer to FIG. 15). Thereafter, the sample images obtained by the CCD camera 435 of the imaging part 430 are sent to the control part 404a of the personal computer 404. As a result, the two-dimensional barcode 10b read by the barcode reading part 420 is associated with the sample images obtained by the CCD camera 435 of the imaging part 420, and the data are stored in the memory 404d of the control part 404a (refer to FIG. 2). Thus, the smear slide corresponding to the obtained sample images can be easily managed.

The sample images (refer to FIG. 15) sent to the control part 404a of the personal computer 404 are subjected to image processing and the blood cells are automatically classified. The obtained analysis results are sent to the control part 404a of the personal computer 404. As a result, the two-dimensional barcode 10b read by the barcode reading part 420 is associated with the analysis results, and the data are stored in the memory 404d of the control part 404a. Thus, the smear slide corresponding to the obtained sample images and the analysis results of the sample can be easily managed.

The imaged slide glass 10 is returned to the feed position 400d in front of the slide chuck 431, and thereafter pushed by the pushing part 415j of the slide glass take-out part 410 so as to be transported along the transport path 400a, as shown in FIG. 14. Thereafter, the empty magazine 450 (refer to FIG. 12) is transported upward from the magazine storage part 441 of the magazine transport part 440, and the slide glass 10 is housed in the first storage part 451 of the magazine 450, as shown in FIG. 17. Then, the imaged glass slides 10 are sequentially housed in the second storage part 451 and third storage part 451 of the magazine 450. The control part 404a of the personal computer 404 controls the number of steps of the motor 443a of the magazine transport part 443. Accordingly, the two-dimensional barcode 10b of the slide glass 10 and the position at which the slide glass 10 is housed in the magazine 450 are associated and stored in the memory 404d of the control part 404a. Thus, the smear slide corresponding to the obtained sample images and the position of the smear slide can be easily managed. The analysis operation of the sample image obtaining system is performed in this way in the present embodiment.

As the described above, the present embodiment provides the sample image obtaining apparatus 400 with a barcode reading part 420 for reading a two-dimensional barcode 10b on a slide glass 10, imaging part 430 for obtaining an image of a sample smeared on a slide glass 10 the two-dimensional barcode 10b of which has been read, and a memory 404d for storing the two-dimensional barcode read by the barcode reading part 420 and the sample image obtained by the imaging part 430 corresponding to the two-dimensional barcode. Thus, the image of the sample smeared on the slide glass 10 obtained by the imaging part 430 can be associated with the two-dimensional barcode 10b specifying the slide glass 10. As a result, the slide glass 10 corresponding to the obtained sample images can be easily managed.

In the present embodiment, the personal computer 404 is provided with the memory 404d for storing the two-dimensional barcode 10b read by the barcode reading part 420 and the position of the slide glass 10 within the magazine 450 corresponding to the two-dimensional barcode 10b. Therefore, after the imaging part 430 obtains the image of the sample smeared on the slide glass 10 the barcode 10b of which has already been read, the slide glass 10 can be housed in the storage part 451 of the magazine 450. If the position of the slide glass 10 is stored in the memory 404d at this time, the position of the stored slide glass 10 can be associated with the sample image of the slide glass 10 and the barcode 10b specifying the slide glass 10. As a result, the slide glass 10 corresponding to the obtained sample images and its position can be easily managed.

In the present embodiment, the personal computer 404 is provided with a control part 404a for performing sample analysis based on the sample image obtained by the imaging part 430. Thus, the blood cells can be readily classified based on the sample image.

In the present embodiment, the personal computer 404 is provided with the memory 404d for storing the two-dimensional barcode 10b read by the barcode reading part 420 and the analysis results corresponding to the two-dimensional barcode 10b wherein the analysis results is obtained by the analysis performed by the control part 404a. Thus, the smear slide corresponding to the obtained sample images and the analysis results of the sample can be easily managed.

In the present embodiment, the smear slide is housed in a cassette 3 in the blood smear slide preparing apparatus 100, the cassette supplying part 300 has the function of storing a plurality of cassettes 3 received from the blood smear slide preparing apparatus 100 and the function of transferring the cassettes 3, and the sample image obtaining apparatus 400 is provided with a slide glass take-out part 410 for taking out a smear slide from a cassette 3 that has been transferred by the cassette supplying apparatus 300. Therefore, the cassette 3 housing the smear slide can be accommodated in the cassette supplying apparatus 300, and can be transported to the slide glass take-out part 410. Then, the smear slide can be removed from the cassette 3 by the slide glass take-out part 410, and the two-dimensional barcode 10b of the smear slide can be easily read by the barcode reading part 430. As a result, the smear slide can be transported while housed in the cassette 3 in the blood smear slide preparing apparatus 100, and the two-dimensional barcode 10b of the slide glass can be easily read.

In the present embodiment, the blood smear slide preparing apparatus 100 is provided with a keeping part 9 for storing a plurality of cassettes 3, second cassette transport part 8 for transporting cassettes 3 to both the cassette supplying apparatus 300 and the keeping part 9, and a control part 110 for controlling whether the second cassette transport part 8 transports the cassette 3 to the cassette supplying apparatus 300 or to the keeping part 9. Therefore, the destination of the slide glass 10 prepared by the blood smear slide preparing apparatus 100 can be automatically determined. The load on the operator is therefore reduced since the operator need not determine the destination of the slide glass 10.

In the present embodiment, the cassette supplying apparatus 300 is provided with a cassette transport part 330 for storing cassettes 3 from which the slide glass 10 has been removed by the slide glass take-out part 410. Therefore, cassettes 3, from which the slide glass 10 has been removed by the slide glass take-out part 410, can be stored. As a result, the operation of removing the cassette 3 is simplified since the operator need not remove the cassette 3 each time a slide glass 10 has been removed from a cassette 3.

In the present embodiment, the cassette supplying apparatus 300 is provided with a cassette transport part 320 for storing a plurality of cassettes 3 received from the blood smear slide preparing apparatus 100, and transporting the stored cassette 3. Thus, a cassette 3 delivered from the blood smear slide preparing apparatus 100 can be easily stored, and transported.

In the present embodiment, the sample image obtaining apparatus 400 is provided with a slide glass take-out part 410, barcode reading part 420, and imaging part 430, and the sample image obtaining apparatus 400 has a function for transporting a slide glass 10 taken out by the slide glass take-out part 410 to the imaging part 430. Thus, the two-dimensional barcode 10b of the slide glass 10 that has been removed from the cassette 3 can easily be read by the barcode reading part 420, and thereafter the image of the slide glass 10 can be obtained by the imaging part 430.

The present embodiment is provided with a blood smear slide preparing apparatus 100 for preparing a smear slide, sample image obtaining apparatus 400 for obtaining a sample image, and a cassette supplying apparatus 300 for supplying the prepared smear slide to the sample image obtaining apparatus 400. Therefore, a smear slide prepared by the blood smear slide preparing apparatus 100 can be automatically transported to the sample image obtaining apparatus 400. Thus, the operation is automated from the preparation of a smear slide to imaging. As a result, the operation from the preparation of a smear slide to imaging is performed efficiently since the time and labor of the user transporting a prepared smear slide manually to the imaging device are unnecessary.

In the present embodiment, the sample image obtaining apparatus 400 is provided with a magazine storage part 441 for storing a plurality of empty magazines 450, a magazine storage part 442 for storing a plurality of magazines 450 containing slide glasses 10, a magazine transport part 443 for transport the empty magazine 450 from the lower magazine storage part 441 to the upper magazine storage part 442, and a magazine feeding part 444 for delivering the magazine 450, which contains slide glasses 10 and was transported upward by the magazine transport part 443, to the magazine storage part 442. Therefore, a plurality of empty magazines 450 for housing imaged slide glasses 10 can be supplied from the magazine storage part 441 accommodating a plurality of empty magazines 450 to the magazine storage part 442, and a plurality of magazines 450 holding imaged slide glasses 10 can be stored to the magazine storage part 442. As a result, the operation of replenishing the magazines 450 is simplified since the user need not open the door 403 to replenish the magazine 450 each time a magazine 450 for housing an imaged slide glass 10 is supplied to the magazine storage part 442. Furthermore, the operation of removing the magazines 450 is simplified since a magazine 450 need not be removed each time a slide glass 10 is housed.

In the present embodiment, the cassette transport part 320 of the cassette supplying apparatus 300 is capable of storing approximately 100 individual cassettes 3. Therefore, a cassette 3 prepared by the blood smear slide preparing apparatus 100 can be stored in the cassette transport part 320 even when the processing power of the blood smear slide preparing apparatus 100 differs from the processing power of the sample image obtaining apparatus 400.

The embodiment disclosed herein is in all aspects simply an example and not to be considered limiting in any way. The scope of the present invention is defined in the scope of the claims and not by the description of the embodiment, and further includes all modifications, meanings and equivalences that fall within the scope of the claims.

For example, in the example of the embodiment described above, the present invention is applied to a sample image obtaining system that includes a blood smear slide preparing apparatus, cassette supplying apparatus, and sample image obtaining apparatus. However, the present invention is not limited to this application inasmuch as the functions of the blood smear slide preparing apparatus, cassette supplying apparatus, and sample image obtaining apparatus may be possessed by a single apparatus.

Furthermore, in the example of the embodiment described above, the present invention is applied to a sample image obtaining system that includes a blood smear slide preparing apparatus, cassette supplying apparatus, and sample image obtaining apparatus. However, the present invention is not limited to this application inasmuch as the blood smear slide preparing apparatus may also possess a function for transporting a cassette to the slide glass take-out part of the sample image obtaining apparatus in a sample image obtaining system configured by a blood smear slide preparing apparatus and a sample image obtaining apparatus. Furthermore, the sample image obtaining apparatus may also possess a function for receiving a cassette from the blood smear slide preparing apparatus, and transporting the received cassette to the slide glass take-out part provided in the sample image obtaining apparatus.

Furthermore, in the example of the embodiment described above, the present invention is applied to a sample image obtaining system that includes a blood smear slide preparing apparatus, cassette supplying apparatus, and sample image obtaining apparatus. However, the present invention is not limited to this application inasmuch as the present invention is applicable to a stand-alone sample image obtaining apparatus.

The above embodiment has been described in terms of a sample image obtaining apparatus provided with a barcode reading part. However, the present invention is not limited to this arrangement inasmuch as the barcode reading part may be provided in the cassette supplying apparatus, and may alternatively be provided in the blood smear slide preparing apparatus. It's preferred that the barcode reading part may be disposed in front of the imaging part so that the barcode reading part can read the barcode on the slide glass just before the image of the sample on the slide glass is obtained by the imaging part.

What is claimed is:

1. A sample image obtaining system, comprising:
a sample smearing apparatus for smearing a sample on a slide glass to form a sample smeared slide glass;
a sample image obtaining apparatus for obtaining an image of the sample smeared on the slide glass; and
a slide glass transferring apparatus for transferring the sample smeared slide glass obtained by the sample smearing apparatus to the sample image obtaining apparatus,
wherein the sample image obtaining apparatus comprises:
an identification information reader configured for reading identification information identifying the sample smeared on the slide glass, the slide glass having the identification information;
an image obtainer configured for obtaining the image of the sample smeared on the slide glass;
a rack setting section for setting a rack having a plurality of housing parts for housing the sample smeared slide glass;
a slide glass inserter for inserting the sample smeared slide glass in one of the plurality of housing parts of the rack after the image of the sample smeared on the slide glass has been obtained by the image obtainer; and
a memory for storing:
the image obtained by the image obtainer;
the identification information read by the identification information reader; and
a position of the housing part in which the sample smeared slide glass is inserted.

2. A sample image obtaining system comprising:
a sample smearing apparatus for smearing a sample on a slide glass to form a sample smeared slide glass;
a sample image obtaining apparatus for obtaining an image of the sample smeared on the slide glass; and
a slide glass transferring apparatus for transferring the sample smeared slide glass obtained by the sample smearing apparatus to the sample image obtaining apparatus,
wherein the sample smearing apparatus comprises a slide glass inserter for inserting the sample smeared slide glass in a cassette, and
wherein the slide glass transferring apparatus comprises:
a cassette accommodating section for accommodating the cassette received from the sample smearing apparatus; and
a cassette transferring section for transferring the cassette accommodated in the cassette accommodating section to a predetermined position,
wherein the sample image obtaining apparatus comprises:
a slide glass take-out part for taking out the sample smeared slide glass from the cassette transferred to the predetermined position;
an identification information reader configured for reading identification information identifying the sample smeared on the slide glass, the slide glass having the identification information;
an image obtainer configured for obtaining the image of the sample smeared on the slide glass; and
a memory for storing the image obtained by the image obtainer and the identification information read by the identification information reader.

3. The sample image obtaining system of claim 2, wherein the sample smearing apparatus comprises:
a second cassette accommodating section for accommodating the cassette after the sample smeared slide glass has been inserted in the cassette by the slide glass inserter;
a second cassette transferring section for transferring the cassette to the slide glass transferring apparatus or to the second cassette accommodating section; and
a controller for controlling whether the second cassette transferring section transfers the cassette to the slide glass transferring apparatus or to the second cassette accommodating section.

4. The sample image obtaining system of claim 2, wherein the slide glass transferring apparatus comprises a third cassette accommodating section for accommodating the cassette after the sample smeared slide glass has been taken out from the cassette by the slide glass take-out part.

5. The sample image obtaining system of claim 2, wherein the sample image obtaining apparatus comprises a slide glass transferring section for transferring the sample smeared slide glass taken out by the slide glass take-out part to the image obtainer.

6. A sample image obtaining system, comprising:
a sample smearing means for smearing a sample on a slide glass;
an identification information reading means for reading identification information identifying the sample smeared on the slide glass, the slide glass being a sample smeared slide glass and having the identification information;
a sample image obtaining means for obtaining an image of the sample smeared on the slide glass;
a slide glass transferring means for transferring the sample smeared slide glass from the sample smearing means to the sample image obtaining means;
a first rack setting means for setting a rack having a plurality of housing parts for housing the sample smeared slide glass;
a slide glass inserting means for inserting the sample smeared slide glass in one of the plurality of housing parts of the rack after the image of the sample smeared on the slide glass has been obtained by the sample image obtaining means; and
a storing means for storing the image obtained by the sample image obtaining means, the identification information read by the identification information reading means, and a position of the housing part in which the sample smeared slide glass is inserted.

7. The sample image obtaining system of claim 6, wherein the sample smearing means comprises the identification information reading means.

8. The sample image obtaining system of claim 6, wherein the slide glass transferring means comprises the identification information reading means.

9. The sample image obtaining system of claim 6, further comprising:
a first rack transferring means for transferring the rack set by the rack setting means to a position where the slide glass inserting means inserts the sample smeared slide glass in the rack;
a second rack setting means for setting the rack after the sample smeared slide glass has been inserted in the rack by the slide glass inserting means; and a second rack transferring means for transferring the rack after the sample smeared slide glass has been inserted in the rack by the slide glass inserting means to the second rack setting means.

10. A method for obtaining a sample image, comprising steps of:
- (a) smearing a sample on a slide glass to form a sample smeared slide glass;
- (b) reading identification information identifying the sample smeared on the slide glass;
- (c) automatically transferring the sample smeared slide glass to a sample image obtaining position;
- (d) obtaining an image of the sample smeared on the slide glass transferred to the sample image obtaining position;
- (e) automatically inserting the sample smeared slide glass in one of a plurality of housing parts of a rack; and
- (f) storing the image, the identification information, and a position of the housing part in which the sample smeared slide glass is inserted.

11. The method of claim 10, wherein the step (b) is performed while the step (c) is being performed.

12. The method of claim 11, wherein the step (c) further comprises the steps of:
- (i) inserting the sample smeared slide glass in a cassette, and
- (ii) taking out the sample smeared slide glass from the cassette, and the step (b) is performed after the sample smeared slide glass has been taken out from the cassette.

13. The method of claim 10, further comprising a step (g) of
analyzing the image of the sample smeared slide glass transferred to the sample image obtaining position.

14. The method of claim 13, wherein the step (f) further stores an analysis result with the image and the identification information.

* * * * *